US008735392B2

(12) United States Patent
Wang et al.

(10) Patent No.: US 8,735,392 B2
(45) Date of Patent: May 27, 2014

(54) CRYSTALLINE (8S,9R)-5-FLUORO-8-(4-FLUOROPHENYL)-9-(1-METHYL-1H-1,2,4-TRIAZOL-5-YL)-8,9-DIHYDRO-2H-PYRIDO[4,3,2-DE]PHTHALAZIN-3(7H)-ONE TOSYLATE SALT

(75) Inventors: Bing Wang, San Jose, CA (US); Daniel Chu, Santa Clara, CA (US); Yongbo Liu, Shanghai (CN); Shichun Peng, Shanghai (CN)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 13/277,607

(22) Filed: Oct. 20, 2011

(65) Prior Publication Data

US 2012/0129865 A1 May 24, 2012

Related U.S. Application Data

(60) Provisional application No. 61/405,476, filed on Oct. 21, 2010.

(51) Int. Cl.
*A01N 43/58* (2006.01)
*A61K 31/495* (2006.01)

(52) U.S. Cl.
USPC .......................................... 514/248; 548/234

(58) Field of Classification Search
USPC .......................................... 514/248; 544/234
See application file for complete search history.

(56) References Cited

U.S. PATENT DOCUMENTS

| 4,526,894 | A | 7/1985 | Enomoto et al. |
| 5,328,905 | A | 7/1994 | Hamminga et al. |
| 6,903,098 | B1 | 6/2005 | Lubisch et al. |
| 7,268,138 | B2 | 9/2007 | Kalish et al. |
| 7,456,178 | B2 | 11/2008 | Kalish et al. |
| 7,601,719 | B2 | 10/2009 | Kalish et al. |
| 7,750,008 | B2 | 7/2010 | Kalish et al. |
| 8,012,976 | B2 | 9/2011 | Wang et al. |
| 8,420,650 | B2 | 4/2013 | Wang et al. |
| 2004/0106631 | A1 | 6/2004 | Bernardelli et al. |
| 2006/0004028 | A1 | 1/2006 | Shiromizu et al. |
| 2008/0058325 | A1 | 3/2008 | Kalish et al. |
| 2009/0088407 | A1 | 4/2009 | Kalish et al. |
| 2010/0035883 | A1* | 2/2010 | Wang et al. ................ 514/248 |
| 2011/0190266 | A1 | 8/2011 | Chu et al. |
| 2011/0190288 | A1 | 8/2011 | Chu et al. |
| 2011/0196153 | A1 | 8/2011 | Wang et al. |
| 2012/0129865 | A1 | 5/2012 | Wang et al. |
| 2013/0053365 | A1 | 2/2013 | Wang et al. |

FOREIGN PATENT DOCUMENTS

| DE | 19727410 A1 | 1/1999 |
| EP | 0927718 A1 | 7/1999 |
| EP | 1340819 A1 | 9/2003 |
| JP | 2001-302669 A | 10/2001 |
| JP | 2002-284699 A | 10/2002 |
| WO | 96/29327 A1 | 9/1996 |
| WO | 99/11645 A1 | 3/1999 |
| WO | 99/59975 A1 | 11/1999 |
| WO | 02/098424 A1 | 12/2002 |
| WO | 2004/080976 A1 | 3/2004 |
| WO | 2004/105700 A1 | 12/2004 |
| WO | 2010/017055 A1 | 2/2010 |
| WO | 2011/097334 A1 | 8/2011 |
| WO | WO 2011/097602 A1 | 8/2011 |
| WO | 2011/130661 A1 | 10/2011 |
| WO | 2011/140009 A1 | 11/2011 |
| WO | 2012/054698 A1 | 4/2012 |

OTHER PUBLICATIONS

ISA, PCT International Search Report and Written Opinion dated Apr. 21, 2011 for International Patent Application No. PCT/US2011/023532.
ISA, PCT International Search Report and Written Opinion dated Apr. 18, 2011 for International Patent Application No. PCT/US2011/023965.
Karlberg et al., "Crystal Structure of the Catalytic Domain of Human PARP2 in Complex with PARP Inhibitor ABT-888," Biochemistry 2010, 49, pp. 1056-1058.
Mendes-Pereira et al., "Synthetic lethal targeting of PTEN mutant cells with PARP inhibitors," EMBO Mol. Med. 2009, 1, pp. 315-322.
ISA, International Search Report dated Apr. 6, 2010 for International Patent Application No. PCT/US2009/051879.
Thomas, et al., "Preclinical selection of a novel poly(ADP-ribose) polymerase inhibitor for clinical trial," Mol. Cancer Ther. 2007, 6(3), pp. 945-956.
United Kingdom Intellectual Property Office, Patents Act I977 Combined Search and Examination Report under Sections 17 & 18(3) dated Nov. 12, 2009 for application No. GB 0913474.3.
United Kingdom Intellectual Property Office, Patents Act 1977 Examination Report under Section 18(3) dated Sep. 14, 2010 for application No. GB 0913474.3.
Science IP, Search Report dated Jan. 9, 2009 (4 total pages).
EPO Supplementary European Search Report dated Feb. 8, 2012 for European Patent Application No. 09805360.6.
Merchant et al., 1987, "Synthesis of Benzoquinolizine Derivatives," Indian Journal of Chemistry 268: 471-472.
ISA, PCT International Search Report and Written Opinion dated Jun. 28, 2011for International Patent Application No. PCT/US2011/032728.
Gaymes et al., 2010, Blood; 52nd Annual Meeting of the American Society of Hematology (ASH), American Society of Hematology, Orlando, FL, USA, 116(21 ): 513, Abstract 1194.
ISA, PCT International Search Report and Written Opinion dated Apr. 27, 2012 for International Patent Application No. PCT/US2011/039045.

(Continued)

*Primary Examiner* — Paul V. Ward
(74) *Attorney, Agent, or Firm* — Jones Day

(57) ABSTRACT

Provided herein are (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt forms, including crystalline forms, and methods of their preparation. Pharmaceutical compositions comprising a (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt are also provided, as are methods of using (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt to treat a disease or condition, such as a cancer.

5 Claims, 19 Drawing Sheets

(56) References Cited

OTHER PUBLICATIONS

Gaymes et al., 2009, Haematologica, Fondazione Ferrata Storti, Rome, IT, 94(5): 638-646.

Ham et al., "Impairment of double-strand breaks repair and aberrant splicing of ATM and MRE11 in leukemia-lymphoma cell lines with microsatellite instability," 2006, Cancer Science, 97(3): 226-234.

Stefanska et al., "2,7-Dihydro-3H-pyridazino[5,4,3-kl]acridin-3-one derivatives, novel type of cytotoxic agents active on multidrug-resistant cell lines. Synthesis and biological evaluation," 2005, Boorganic & Medicinal Chemistry, 3 (6):1969-75.

CAS Reg. No. 1283718-99-9, Chemical Name "5-Quinolinecarboxylic acid, 1,2,3,4-tetrahydro-4-oxo-2-trifluoromethyl)-methyl ester," 2012.

ISA, PCT International Search Report and Written Opinion dated Nov. 30, 2011 for International Patent Application No. PCT/US2011/057039.

* cited by examiner

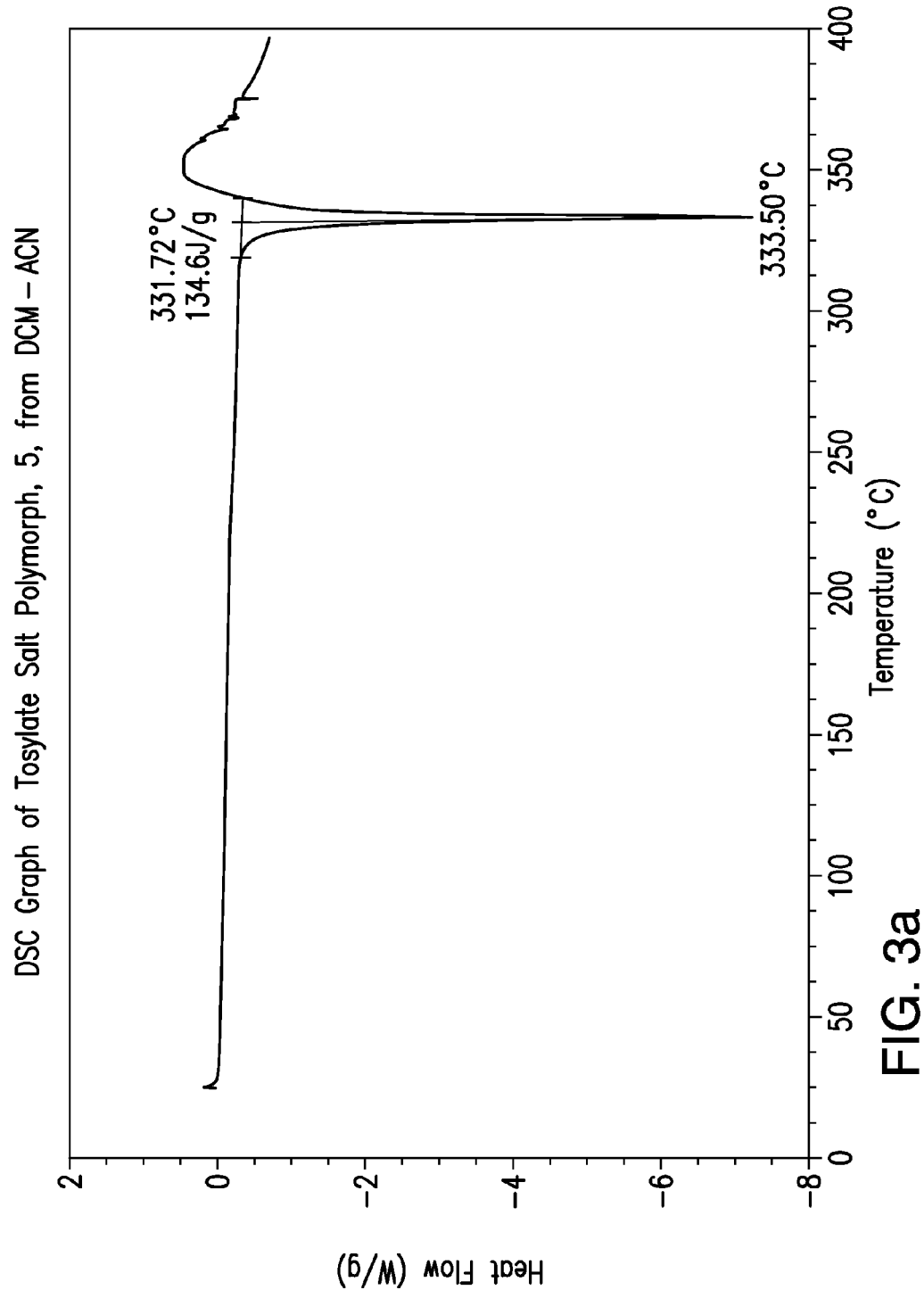

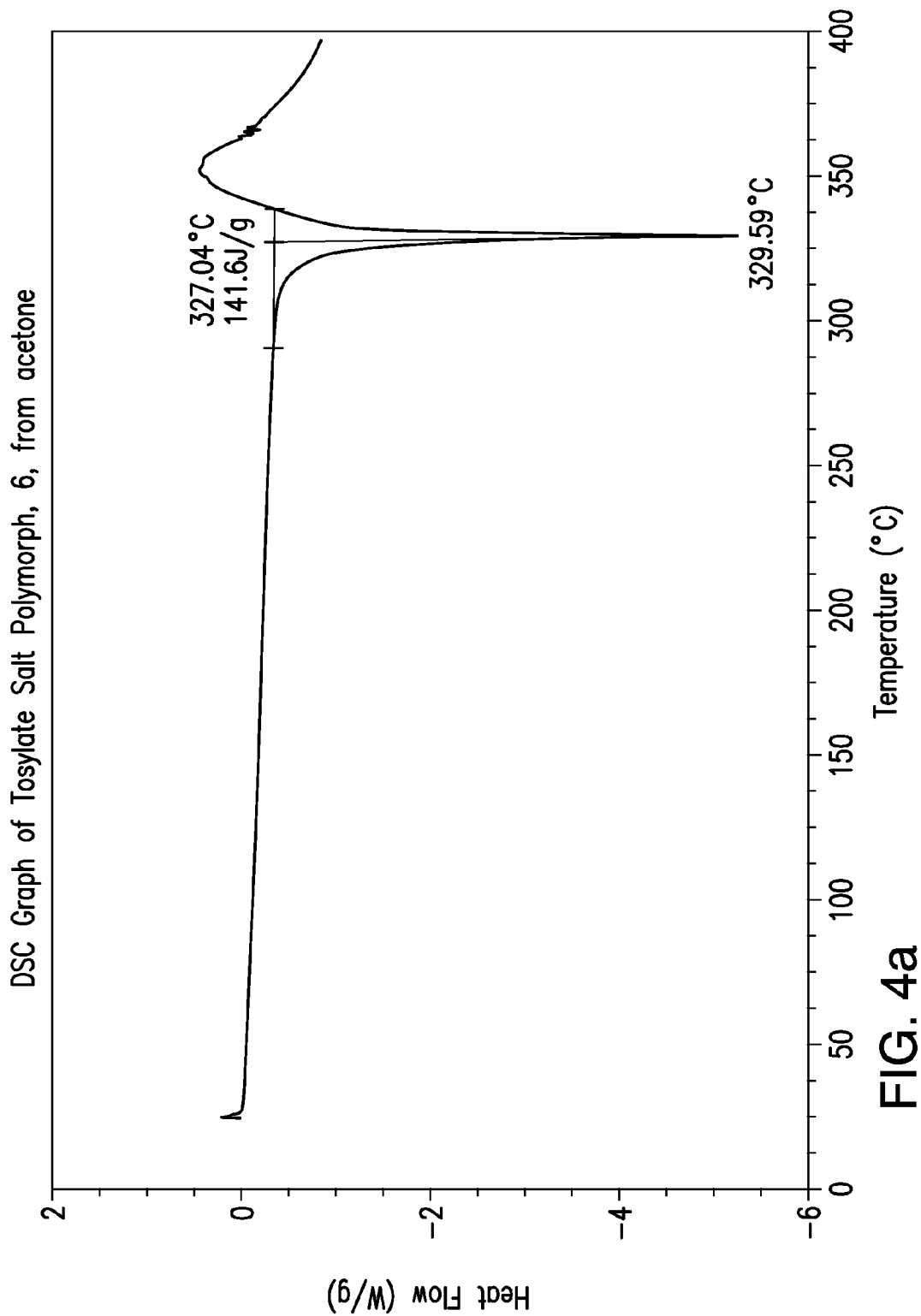

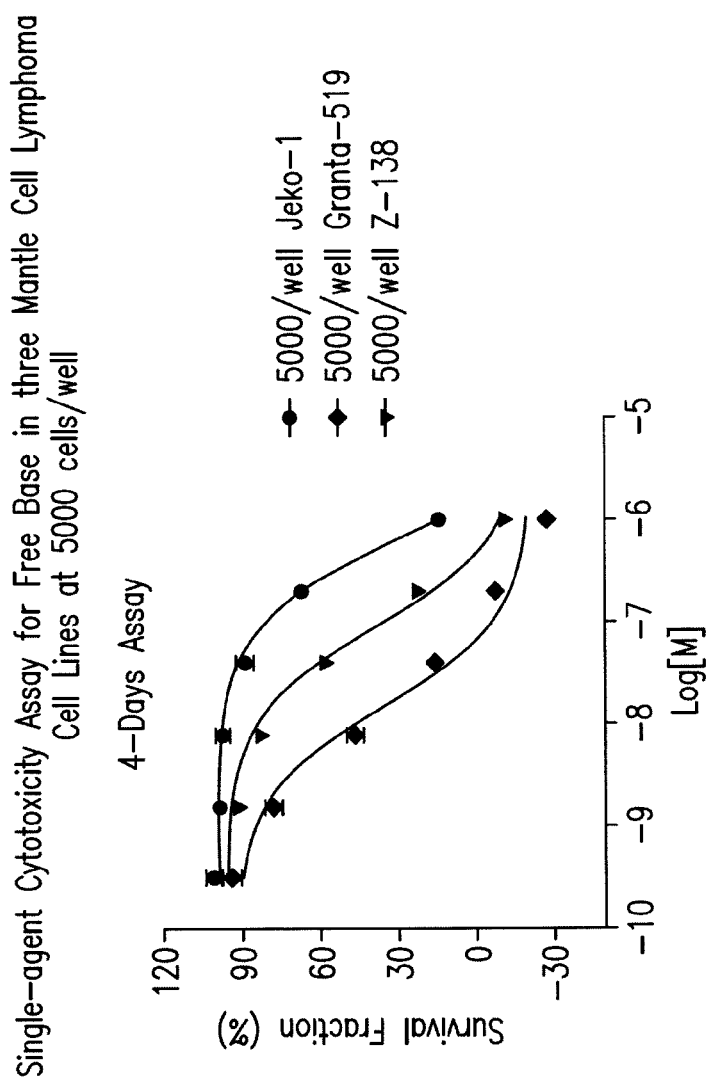

CRYSTALLINE (8S,9R)-5-FLUORO-8-(4-FLUOROPHENYL)-9-(1-METHYL-1H-1,2,4-TRIAZOL-5-YL)-8,9-DIHYDRO-2H-PYRIDO[4,3,2-DE]PHTHALAZIN-3(7H)-ONE TOSYLATE SALT

CROSS REFERENCE TO RELATED APPLICATIONS

The present application claims the benefit of priority of U.S. Provisional Application No. 61/405,476, filed Oct. 21, 2010, the content of which is hereby incorporated by reference in its entirety.

TECHNICAL FIELD

This application relates to (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt forms, including crystalline forms; methods of preparing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one and tosylate salt forms thereof; and pharmaceutical compositions comprising a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt form.

BACKGROUND

Enzymes in the poly(ADP-ribose)polymerase (PARP) protein family participate in a number of cellular functions including assisting in the repair of DNA damage. Inhibiting PARP activity is a promising therapeutic approach to treatment of certain cancers. A number of PARP inhibitors are in clinical and preclinical stages as candidate drugs for treatments of ovarian, breast, colorectal, prostate and other cancers. A class of PARP inhibitors disclosed in U.S. Pub. No. 2010/0035883 includes (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. Preclinical studies indicate that this compound may be a useful therapy for some cancer patients.

U.S. Pub. No. 2010/0035883 provides a synthesis of 5-fluoro-8-(4-fluorophenyl)-9-(1-methyl-1H-1,2,4-triazol-5-yl)-8,9-dihydro-2H-pyrido[4,3,2-de]phthalazin-3(7H)-one and chiral resolution of its (8S,9R) enantiomer. See, e.g., U.S. 2010/0035883, Examples 94 and 155, incorporated herein by reference in its entirety for all purposes. Additional methods of preparing the compound are described in WO 2011/097602. To move a drug candidate such as (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one to a viable pharmaceutical product, it can be important to understand whether the drug candidate has polymorph forms, as well as the relative stability and interconversions of these forms under conditions likely to be encountered upon large-scale production, transportation, storage and pre-usage preparation. The ability to control and produce a stable polymorph with a robust manufacturing process can be key for regulatory approval and marketing. Large scale production processes for high purity 5-fluoro-8-(4-fluorophenyl)-9-(1-methyl-1H-1,2,4-triazol-5-yl)-8,9-dihydro-2H-pyrido[4,3,2-de]phthalazin-3(7H)-one are sought, which is hampered by the fact that parameters affecting the stability of this compound are not known and polymorphic forms of the compound have not been available.

BRIEF SUMMARY

In one aspect, provided herein is a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In some embodiments the tosylate salt is in a crystalline form. In some embodiments, provided herein are solid forms of a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, including crystalline forms, amorphous forms, or mixtures thereof.

In another aspect, provided herein are methods of synthesizing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one in a free base form ("free base").

In another aspect, a method of preparing a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is provided. In certain embodiments, the tosylate salt is prepared from a suspension in tetrahydrofuran (THF).

In another aspect, the present application provides a pharmaceutical composition comprising a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, or a solid form thereof, as described herein.

In another aspect, the present application provides a method of treating cancer with a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, in another example a crystalline form thereof, or a composition thereof.

DESCRIPTION OF THE DRAWINGS

FIG. 3a provides a DSC graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 5, from DCM-ACN preparation.

FIG. 4a provides a DSC graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 6, from acetone preparation.

Figure 6:
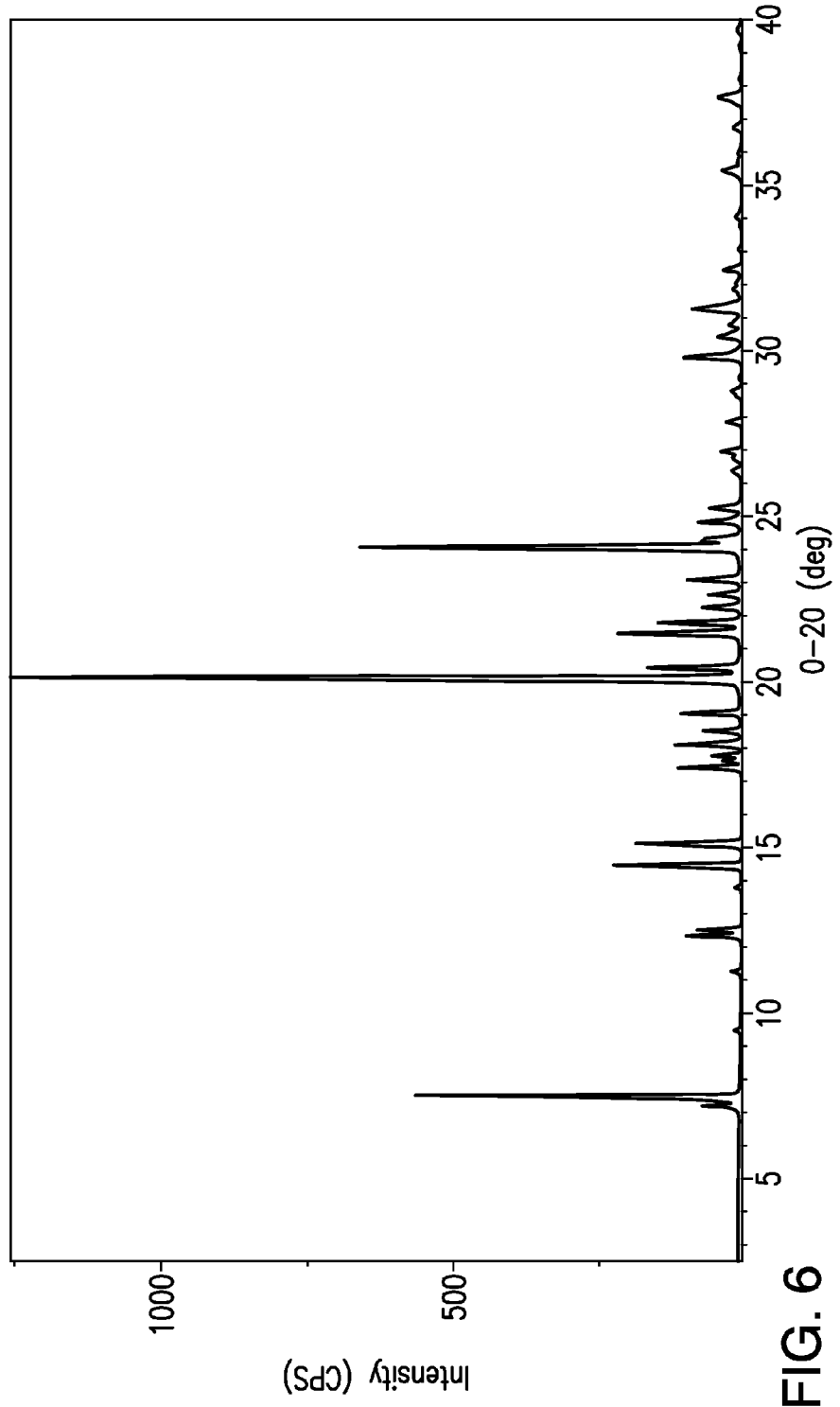

FIG. 6 provides an X-ray powder diffraction (XRPD) spectrogram of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph.

Figure 7A:
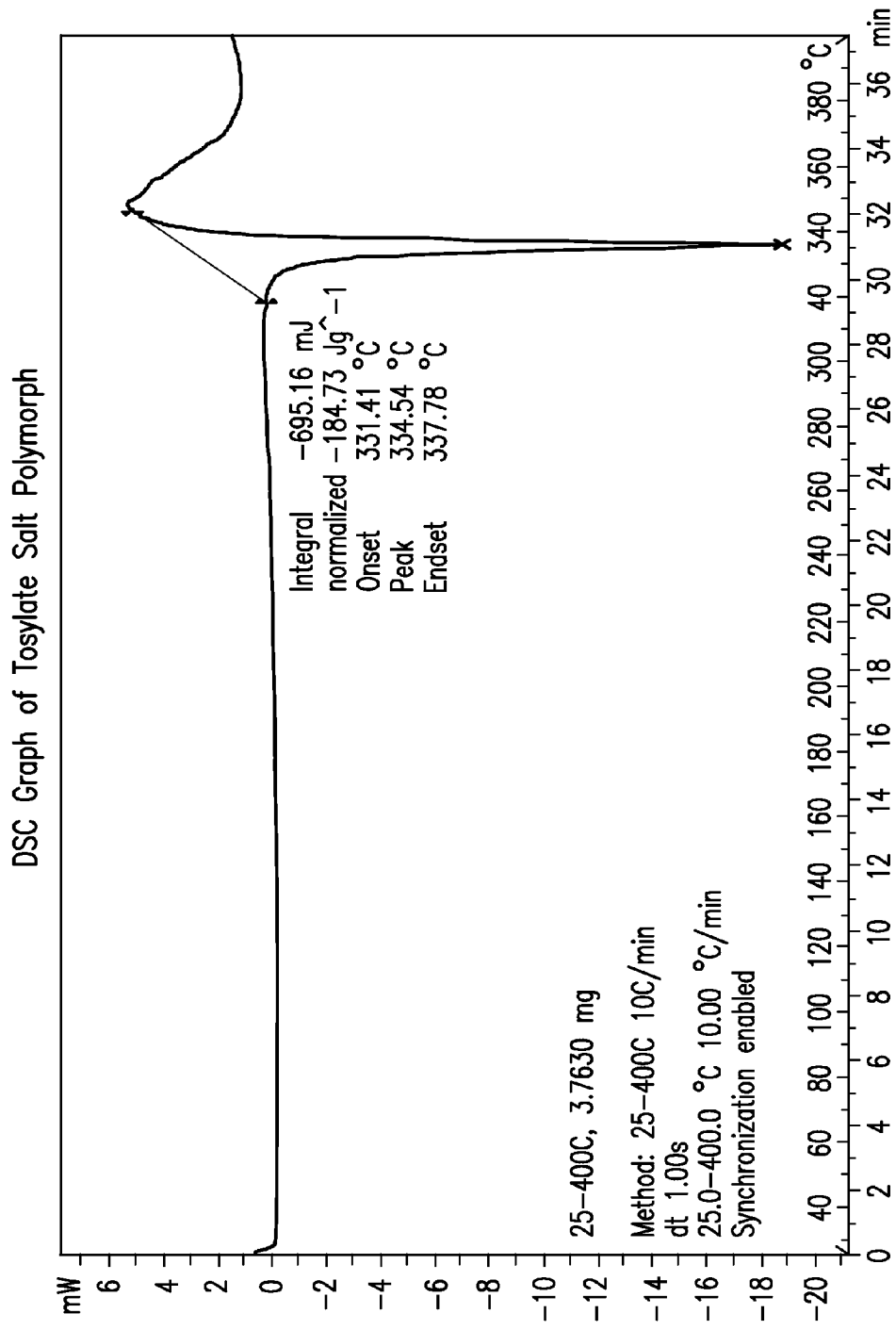

FIG. 7a provides a DSC graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7M-one tosylate salt polymorph.

Figure 7B:
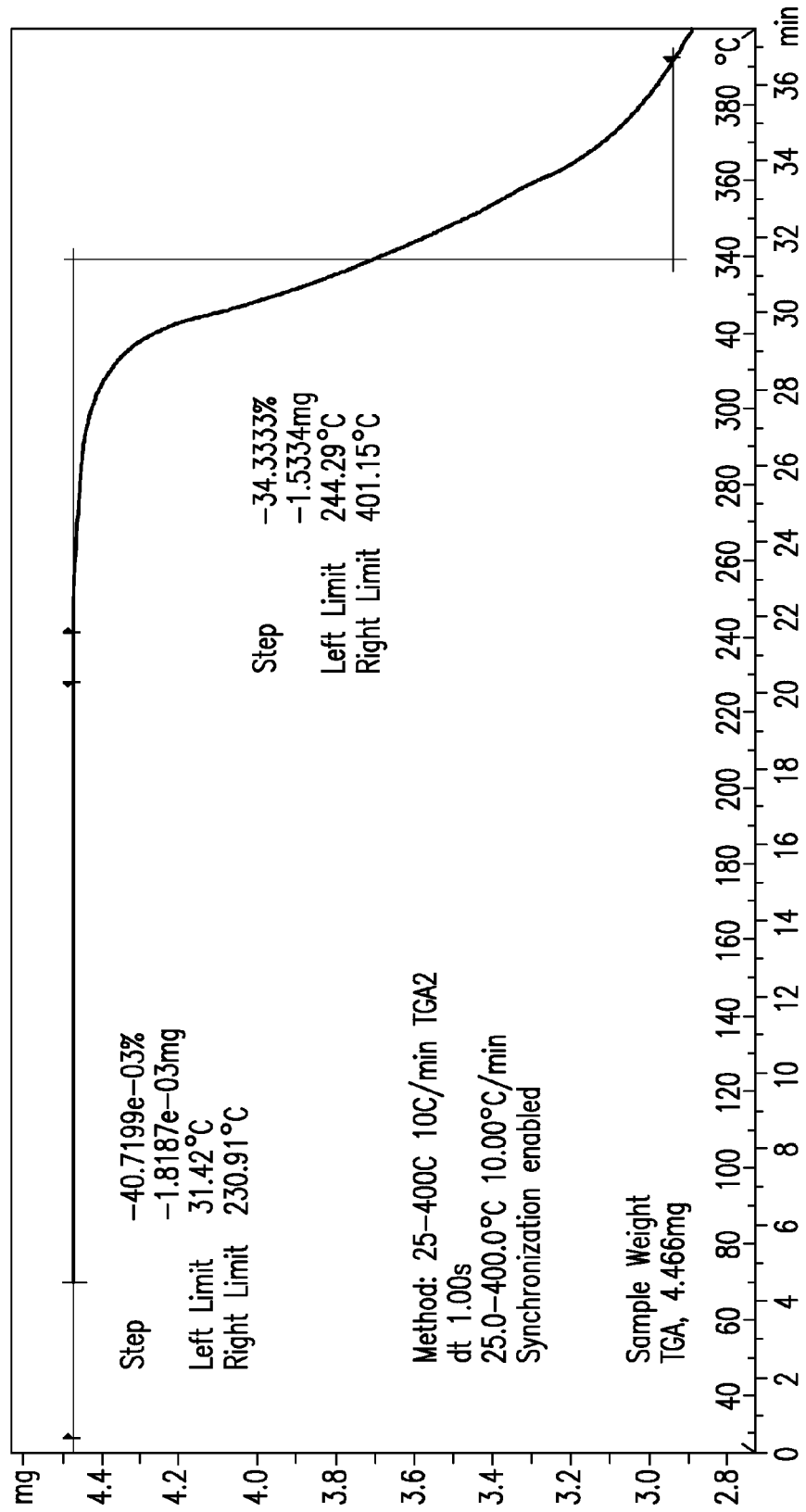

FIG. 7b provides a TGA graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph.

Figure 8:
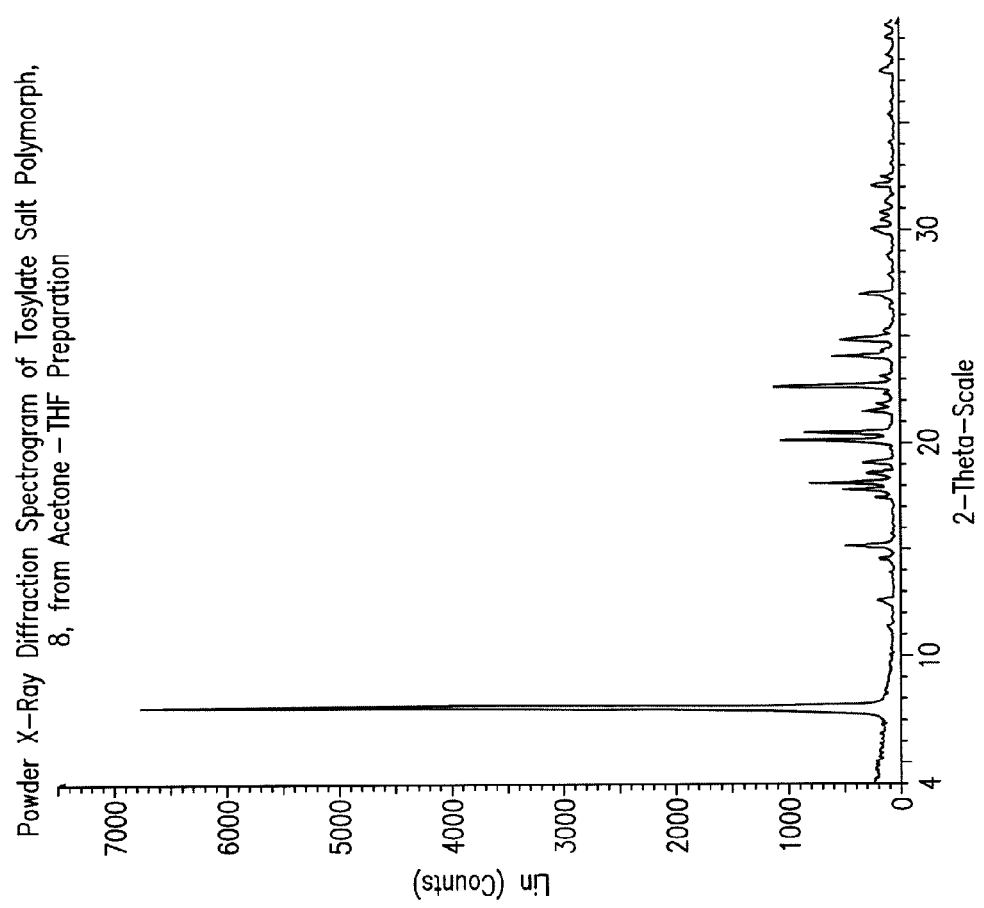

FIG. 8 depicts an X-ray powder diffraction (XRPD) spectrogram of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 8, from acetone-THF preparation.

Figure 9:
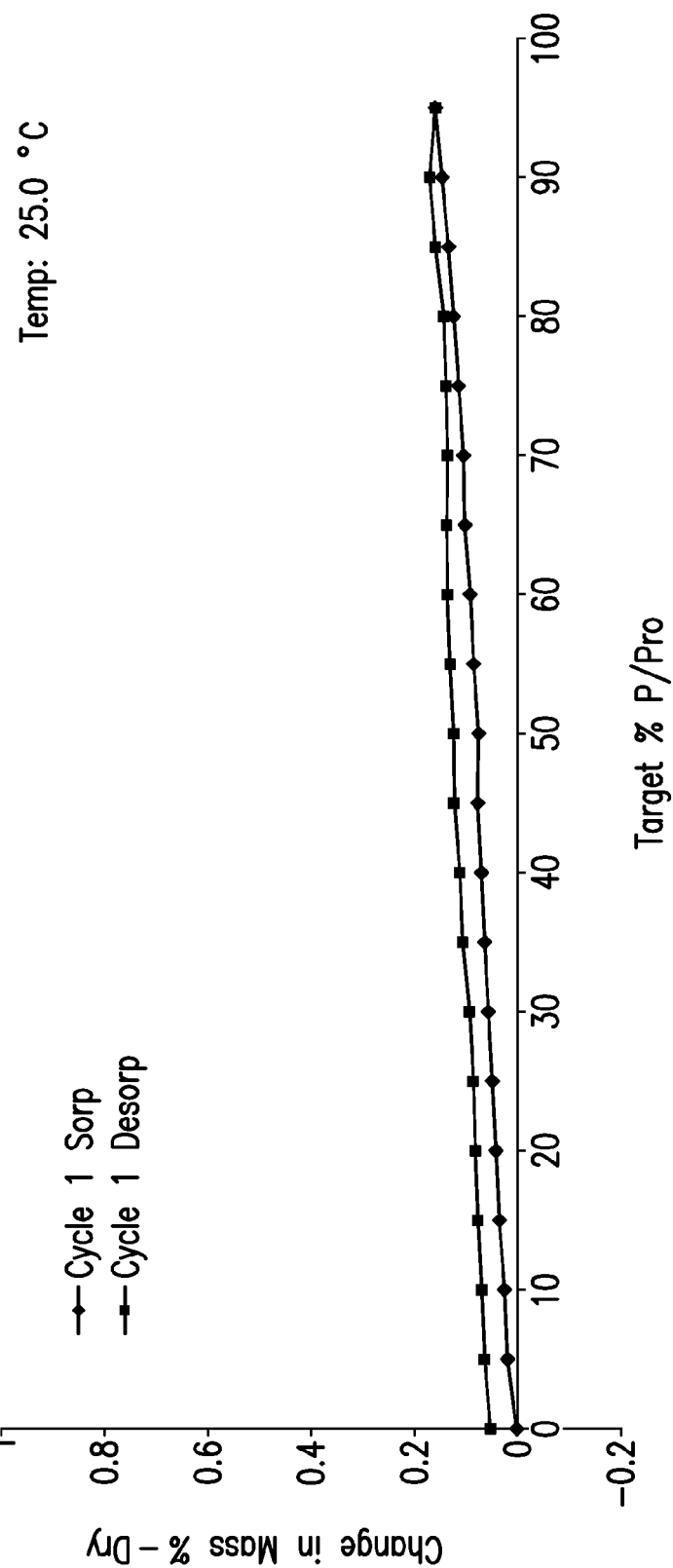

FIG. 9 provides a dynamic vapor sorption isotherm plot of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 8, from acetone-THF preparation.

Figure 10A:
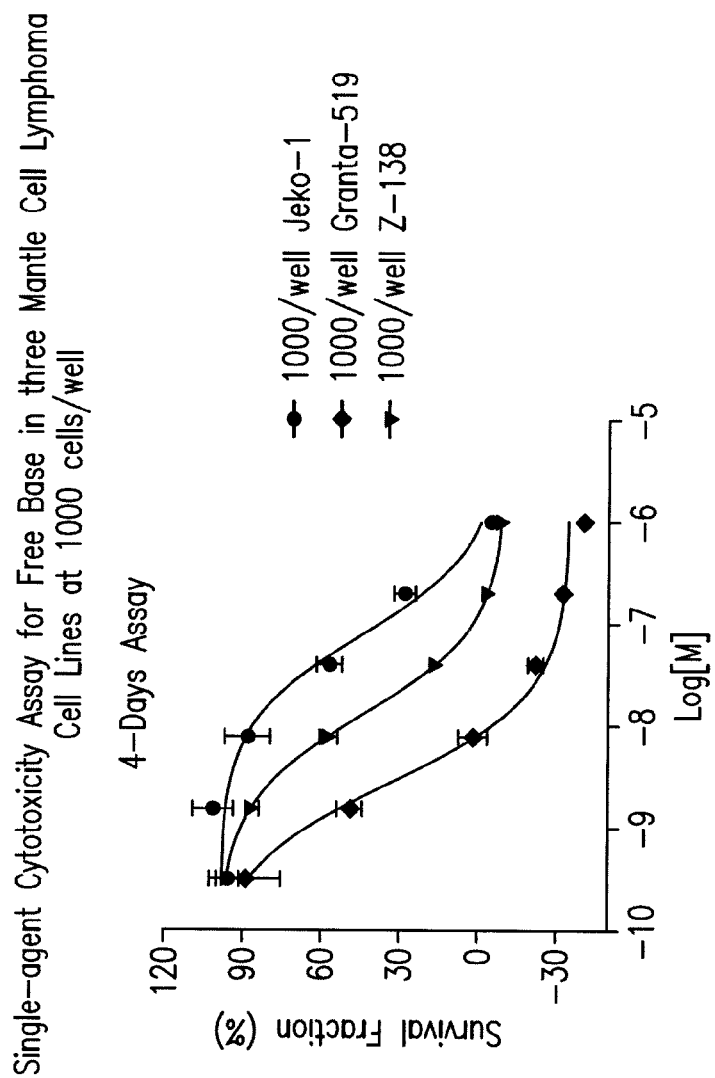

FIG. 10a provides data for a single-agent cytotoxicity assay for free base in three mantle cell lymphoma cell lines at 1000 cells/well.

FIG. 10b provides data for a single-agent cytotoxicity assay for free base in three mantle cell lymphoma cell lines at 5000 cells/well.

Figure 11A:
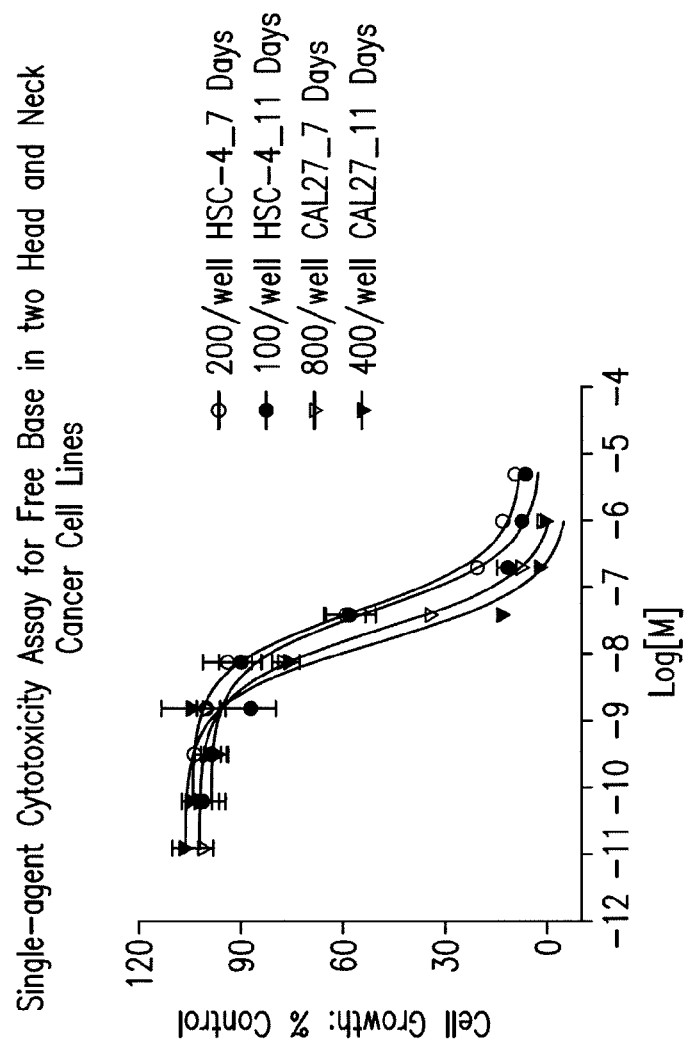

FIG. 11a provides data for a single-agent cytotoxicity assay for free base in two head and neck cancer cell lines.

Figure 11B:
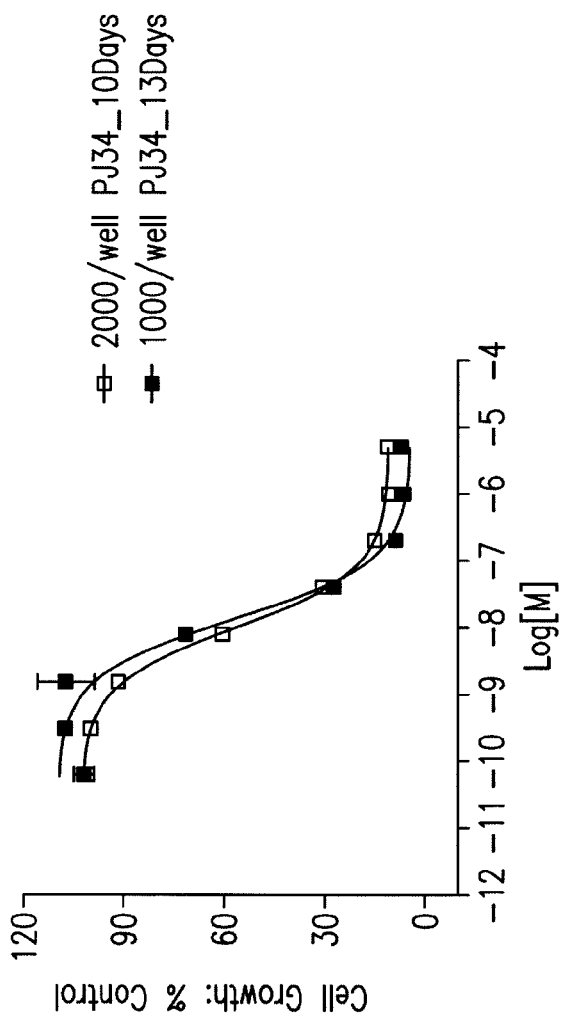

FIG. 11b provides data for a single-agent cytotoxicity assay for free base in PE/CA-PJ34 head and neck cancer cell line.

Figure 12:
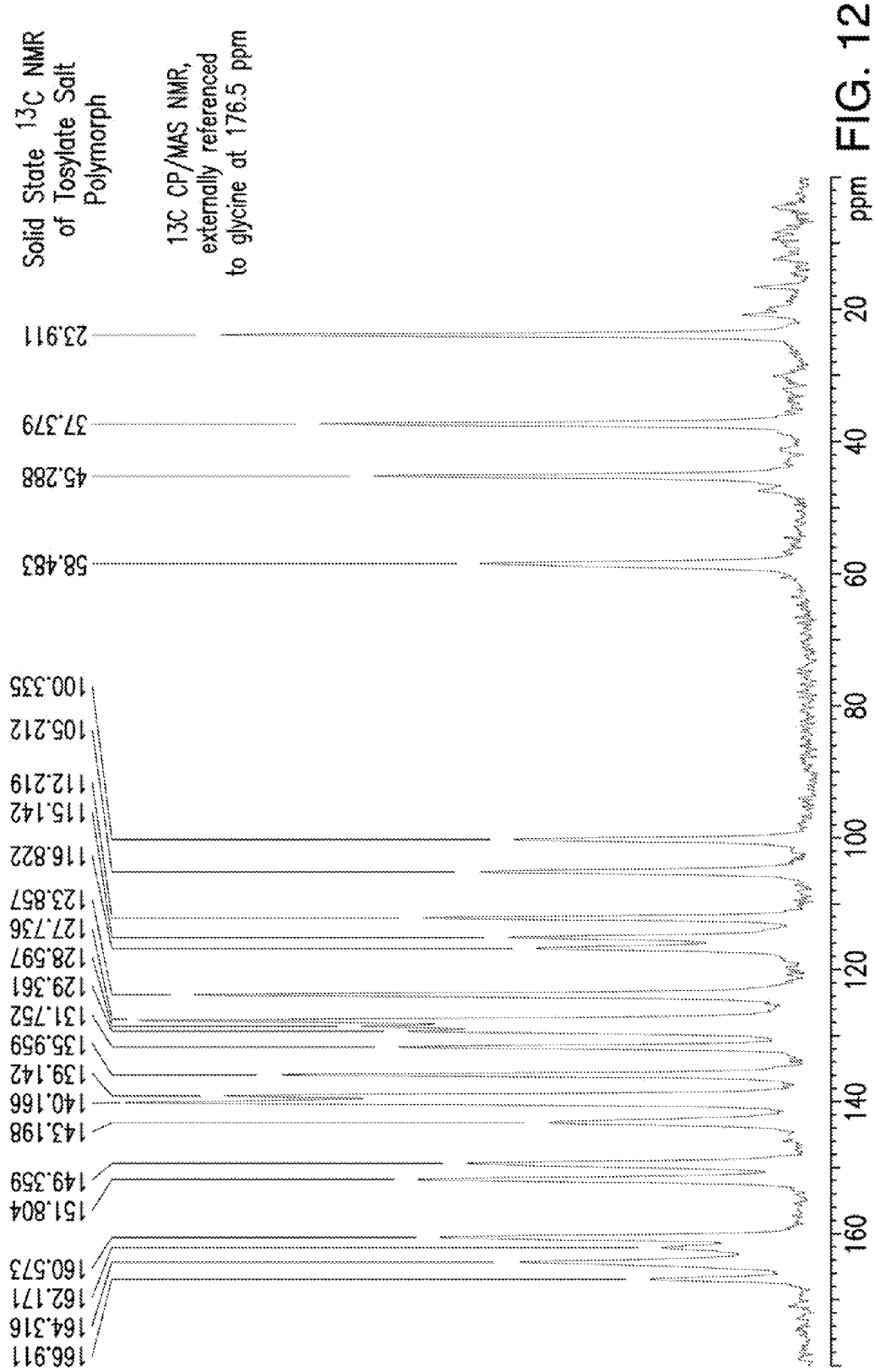

FIG. 12 provides a solid state $^{13}C$ NMR spectrum for a (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph.

DETAILED DESCRIPTION (8S,9R)-5-Fluoro-8-(4-fluorophenyl)-9-(1-methyl-1H-1,2,4-triazol-5-yl)-8,9-dihydro-2H-pyrido[4,3,2-de]phthalazin-3(7H)-one is a promising candidate drug for the treatment of cancers including, for instance, leukemia (including acute myelogenous leukemia, chronic lymphocytic leukemia), myelodysplastic syndrome, colon cancer, EBV-associated tumors (including Burkitt's lymphoma, nasopharyngeal carcinoma, lymphomas in AIDS patients, smooth muscle tumors in AIDS patients, Hodgkin's disease, non-Hodgkin's lymphoma, lymphoproliferative disease in immunosuppressed patients, leiomyosarcomas in immunosuppressed patients, EBV+ gastric cancer, EBV+ breast cancer, T-cell lymphoma), endometrial cancers (including carcinomas and sarcomas), gastrointestinal stromal tumor, gliomas, glioblastoma, lymphoma (including mantle cell lymphoma), melanoma, breast (including metastatic, BRCA-positive, and BRCA-negative), ovarian (including advanced, high grade serous, platinum-sensitive, platinum-resistant, platinum-refractory, and BRCA-negative), cervical, pancreatic (including BRCA-negative), peritoneal, prostate (including BRCA-negative, metastatic, and castration resistant), hereditary nonpolyposis colon cancer (HNPCC), lung cancer (including non small cell lung carcinoma, small cell lung carcinoma), colorectal carcinomas, uterine carcinosarcoma, solid tumors (such as those of the bladder, bowel, brain, breast, endometrium, heart, kidney, lung, cancer of non-pancreatic endocrine organ (thyroid), and head and neck), and hematological tumors.

Provided herein are methods of producing the compound, including a tosylate salt form of the compound. The methods provided herein provide, for example, improved recoveries of product and/or fewer processing steps, amenable to large scale production of the compound, as compared to previously reported syntheses of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one in its free base form (see, e.g., US 2010/0035883). In one embodiment, as demonstrated in the examples that follow below, a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one has been prepared in a crystalline form having stability exceeding that of other solid forms associated with the free base and other salts of the compound, or having other beneficial properties. The examples provided herein demonstrate that certain different solvents can be used to form a tosylate salt polymorph of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one.

Terminology

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

| Abbreviations | |
|---|---|
| Abbreviation | Meaning |
| ACN or CH$_3$CN | acetonitrile |
| DCM | dichloromethane |
| DSC | differential scanning calorimetry |
| DVS | dynamic vapor sorption |
| eqiv. | equivalent |
| ESI | electron spray ionization |
| EtOAc | ethyl acetate |
| g | gram |
| GMP | good manufacturing practices |
| h | hour |
| HPLC | high performance liquid chromatography |
| IR | infrared |
| kg | kilogram |
| LC-MS | liquid chromatography - mass spectrometry |
| m | minute |
| MeOH | methanol |
| mg | milligram |
| min | minute |
| mL | milliliter |
| mmol | millimole |
| MHz | megahertz |
| MPa | megapascal |
| MS | mass spectrometry |
| MTBE | methyl tert-butyl ether |
| NMR | nuclear magnetic resonance |
| PARP | poly(ADP-ribose)polymerase |
| ppm | parts per million |
| PSA | particle size analysis |
| PTEN | phosphatase and tensin homolog |
| RH | relative humidity |
| SEM | scanning electron microscopy |
| TGA | thermogravimetric analysis |
| THF | tetrahydrofuran |

| Abbreviations | |
|---|---|
| Abbreviation | Meaning |
| TsOH | p-toluenesulfonic acid |
| UV | ultraviolet |
| XRPD | X-Ray Powder Diffraction |

As used herein, a reference to "(8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one" or to its formula,

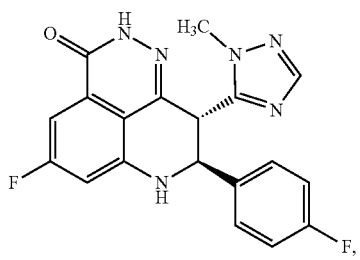 [SMILES: Cn1ncnc1[C@H]1c2n[nH]c(=O)c3cc(F)cc(c23)N[C@@H]1c1ccc(F)cc1]

will, unless otherwise noted or made clear in the context in which the reference is used, be a reference to the free base form of the compound.

It will be understood that a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one comprises a cation of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (e.g., in one embodiment, protonated at one atomic position, or in other embodiments, protonated at more than one atomic position) and an anion of p-toluenesulfonic acid, where the anion is referred to herein as "tosylate." In certain embodiments, solid forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt will comprise a cation to anion molar ratio of about 1:1. In certain embodiments, the cation to anion molar ratio in the solid salt will be about 1:1.33, about 1:1.5 or about 1:2.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

As used herein, and unless otherwise specified, the terms "about" and "approximately," when used in connection with a numeric value or range of values which is provided to describe a particular solid form, e.g., a specific temperature or temperature range, such as, for example, that describing a melting, dehydration, desolvation or glass transition; a mass change, such as, for example, a mass change as a function of temperature or humidity; a solvent or water content, in terms of, for example, mass or a percentage; or a peak position, such as, for example, in analysis by, for example, $^{13}C$ NMR, DSC, TGA and XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form.

The term "amorphous" or "amorphous form" is intended to mean that the substance, component, or product in question is not substantially crystalline as determined, for instance, by XRPD or where the substance, component, or product in question, for example is not birefringent when viewed microscopically. In certain embodiments, a sample comprising an amorphous form of a substance may be substantially free of other amorphous forms and/or crystalline forms.

The term "crystalline form" or "crystal form" refers to a crystalline solid form of a chemical compound, including, but not limited to, a single-component or multiple-component crystal form, e.g., a polymorph of a compound; or a solvate, a hydrate, a clathrate, a cocrystal, a salt of a compound, or a polymorph thereof. The term "crystal forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal countermolecules, desolvation, dehydration, rapid evaporation, rapid cooling, slow cooling, vapor diffusion, sublimation, grinding and solvent-drop grinding.

Techniques for characterizing crystal forms and amorphous forms include, but are not limited to, TGA, DSC, XRPD, single crystal X-ray diffractometry, vibrational spectroscopy, e.g., IR and Raman spectroscopy, solid-state NMR, optical microscopy, hot stage optical microscopy, SEM, electron crystallography and quantitative analysis, PSA, surface area analysis, solubility studies and dissolution studies.

As used herein and unless otherwise indicated, the term "hydrate" means a compound or salt thereof, further including a stoichiometric or non-stoichiometric amount of water bound by non-covalent intermolecular forces. As used herein and unless otherwise indicated, the term "solvate" means a solvate formed from the association of one or more solvent molecules to a compound provided herein or salt thereof. The term "solvate" includes hydrates (e.g., hemihydrates, monohydrate, dihydrate, trihydrate, tetrahydrate, and the like). The solvates (e.g. hydrates) of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one can be crystalline or non-crystalline.

The term "pharmaceutically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

The term "polymorph" or "polymorphic form" refers to one of two or more crystal forms that comprise the same molecule, molecules or ions. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs).

As used herein and unless otherwise indicated, the term "stereomerically pure" means a composition that comprises one stereoisomer of a compound and is substantially free of other stereoisomers of that compound. In certain embodiments, stereomerically pure (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is provided herein that is substantially free of the other stereoisomers including, for example, (8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In certain embodiments, a stereomerically pure compound comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, greater than about 97 percent by weight of one stereoisomer of the compound and less than about 3 percent by weight of the other stereoisomers, or greater than about 99 percent by weight of one stereoisomer of the compound and less than about 1 percent by weight of the other stereoisomers of the compound. In certain embodiments, term "stereomerically pure" (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one means that the compound is made up of approximately 100% by weight of this particular stereoisomer. The above percentages are based on the total amount of combined stereoisomers of the compound.

As used herein, a crystalline or amorphous form that is "pure," i.e., substantially free of other crystalline or amorphous forms, contains less than about 10 percent by weight of one or more other crystalline or amorphous form, less than about 5 percent by weight of one or more other crystalline or amorphous form, less than about 3 percent by weight of one or more other crystalline or amorphous form, less than about 1 percent by weight of one or more other crystalline or amorphous form, or less than about 0.5 percent by weight of one or more other crystalline or amorphous form. In certain contexts, as used herein, "substantially pure" (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof can mean free of other chemical compounds, for example, unreacted precursors and side products that might be present in process for preparing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In other contexts, as used herein, a "substantially pure" solid form (e.g., crystalline form or amorphous form) of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof can mean free of other solid forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or salts or solvates thereof. As such, "substantially pure" (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one may comprise, in certain embodiments, less than about 10%, 5%, 3%, 2%, 1%, 0.75%, 0.5%, 0.25%, or 0.1% by weight of one or more other crystal forms and amorphous forms of the compound and/or other chemical compounds. In certain embodiments, a solid form that is substantially pure is substantially free of one or more other particular crystal forms, amorphous forms, and/or other chemical compounds.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment" are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response being sought by a researcher, veterinarian, medical doctor, or clinician, for example, to inhibit PARP activity in vivo, to inhibit cancer cell growth and/or proliferation, and/or to decrease cancer cell numbers.

As used herein the term "vol" or "vols" means a weight/volume ratio of solid reactants to liquid solvents. For example, 250 g of a solid substance in 10 vols of a solvent means the substance is dissolved in 10×250 mL, or 2.5 L, of solvent.

Embodiments

In one aspect, provided herein is a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one.

In some embodiments, the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one tosylate salt provided herein is in a crystalline form. In some embodiments, the crystalline form is unsolvated. In other embodiments, the crystalline form is a solvate. For instance, a crystalline solvate form may be a hydrate. In other embodiments, the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt provided herein is in an amorphous form. In other embodiments, provided herein is a solid form (e.g., a crystalline form, an amorphous form, or a mixture of forms) of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof (e.g., a salt provided herein elsewhere). In one embodiment, provided herein is a crystalline form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof. In one embodiment, provided herein is an amorphous form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof.

In certain embodiments, the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate crystalline salt form provided herein is substantially pure. For instance, in various embodiments, the crystalline tosylate salt purity is of at least about 90%, at least about 95%, at least about 97%, at least about 98%, at least about 99%, at least about 99.2%, at least about 99.5%, at least about 99.6%, at least about 99.7% or at least about 99.8% by weight of a single crystalline form, the remainder of the total weight which may be other crystalline or amorphous forms and/or other compounds. In one embodiment, the crystalline tosylate salt is essentially a single-component crystalline form or a single polymorph. In another embodiment, the crystalline tosylate salt is a multiple-component crystalline form comprising a first crystalline form and at least one other crystalline and/or amorphous form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In some or any embodiments, the crystalline form is substantially free of an amorphous form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one.

Unless otherwise specified, when an XRPD peak is expressed in 2θ angle degrees, it should be understood that copper Kα1 radiation is used. In some embodiments, the 2θ angle degrees value provided herein may vary to an extent of about ±0.2°θ, while still describing the same XRPD peak.

In the $^{13}$C solid state NMR, the peak positions can vary depending on factors such as signal-to-noise ratio, peak width, temperature, spinning speed, decoupling efficiency, magic angle setting, data processing procedures and parameters, and software peak picking algorithm. In addition, peak position is relative to the chemical shift referencing procedure. Several different chemical shift reference standards may be used and will not necessarily give the same results. This may lead to peak positions that are different by several ppm. However, typically all of the peaks will have a systematic change in position in the same direction if a different reference standard was used or if the analyst used a different value for the reference peak position of the same standard. In some embodiments, the ppm values in the $^{13}$C solid state NMR provided herein may vary to an extent of about ±0.2 ppm, while still describing the same peak.

In certain embodiments, a crystalline salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is provided having an XRPD pattern comprising one or more (e.g. one, two, three, four, five, six, seven, eight, nine, ten, or greater than ten; or at least three, at least four, at least five, at least six, or at least seven) characteristic peaks selected from peaks expressed in d-values (Å) according to any one of Tables 9, 11, 13, 15, 17 and 25. In another embodiment, the crystalline salt is a tosylate salt having one or more (e.g., one, two, three, four, five, six, seven, eight, nine, ten, or greater than ten; or at least three, at least four, at least five, at least six, or at least seven) XRPD peaks selected from peaks with 2θ angle degrees according to any one of Tables 9, 11, 13, 15, 17 and 25. In certain embodiments, the crystalline tosylate salt has an XRPD pattern substantially as provided in FIG. 1, 6, or 8.

In certain embodiments, the crystalline tosylate salt provided herein has an XRPD pattern comprising one or more (e.g., one, two, three, four, five, six, seven, eight, nine, ten, or greater than ten; or at least three, at least four, at least five, at least six, or at least seven) XRPD peaks selected from peaks with 2θ angle degrees or d values (Å) as provided in Table 15. In some embodiments, the crystalline tosylate salt has XRPD pattern comprising one or more peaks (e.g., at least three, at least four, at least five, at least six, or at least seven peaks) selected from peaks with d values (Å) of about 11.79, 5.86, 4.90, 4.42, 4.35, 3.93, and 3.70. In some embodiments, the crystalline tosylate salt has XRPD pattern comprising one or more peaks (e.g., at least three, at least four, at least five, at least six, or at least seven peaks) selected from peaks with d values (Å) of about 11.79; 5.86; 4.90; 4.65; 4.42; 4.35; 4.13; 3.93; and 3.70. Within certain embodiments, the XRPD pattern of the crystalline tosylate salt comprises one or more peaks (e.g., at least three, at least four, at least five, at least six, or at least seven peaks) selected from peaks with d values (Å) of about 11.79; 5.86; 4.98; 4.90; 4.79; 4.65; 4.42; 4.35; 4.13; 3.93; 3.70; and 3.58. In certain embodiments, the XRPD pattern of the crystalline tosylate salt comprises one or more peaks (e.g., at least three, at least four, at least five, at least six, or at least seven peaks) selected from peaks with d values (Å) comprise 11.79; 7.07; 6.13; 5.86; 5.10; 4.98; 4.90; 4.79; 4.65; 4.42; 4.35; 4.13; 4.08; 3.93; 3.85; 3.70; 3.58; 3.31; and 2.99. In some embodiments, the crystalline tosylate salt has an XRPD pattern comprising one or more peaks (e.g., at least three, at least four, at least five, at least six, or at least seven peaks) selected from peaks with 2θ angle degrees of about 7.49, 15.10, 18.10, 20.06, 20.40, 22.61, and 24.01. In some embodiments, the crystalline tosylate salt has an XRPD pattern comprising one or more peaks (e.g., at least three, at least four, at least five, at least six, or at least seven peaks) selected from peaks with 2θ angle degrees of about 7.49, 15.10, 18.10, 19.08, 20.06, 20.40, 21.49, 22.61, and 24.01. In some embodiments, the crystalline tosylate salt has an XRPD pattern comprising one or more peaks (e.g., at least three, at least four, at least five, at least six, or at least seven peaks) selected from peaks with 2θ angle degrees of about 7.49, 15.10, 17.78, 18.10, 18.49, 19.08, 20.06, 20.40, 21.49, 22.61, 24.01, and 24.84. In some embodiments, the crystalline tosylate salt has an XRPD pattern comprising one or more peaks (e.g., at least three, at least four, at least five, at least six, or at least seven peaks) selected from peaks with 2θ angle degrees of about 7.49, 12.50, 14.44, 15.10, 17.38, 17.78, 18.10, 18.49, 19.08, 20.06, 20.40, 21.49, 21.76, 22.61, 23.05, 24.01, 24.84, 26.93, and 29.82.

In certain embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 15. In some embodiments, the crystalline tosylate salt has an XRPD pattern comprising one or more peaks (e.g., at least three, at least four, at least five, at least six, or at least seven peaks) selected from peaks with d values (Å) of about 11.8, 5.9, 4.9, 4.42, 4.35, 3.9, and 3.7. In some embodiments, the crystalline tosylate salt has an XRPD pattern comprising one or more peaks (e.g., at least three, at least four, at least five, at least six, or at least seven peaks) selected from peaks with d values (Å) of about 11.8; 5.9; 4.9; 4.7; 4.42; 4.35; 4.1; 3.9; and 3.7. Within certain embodiments, the XRPD pattern comprises one or more peaks (e.g., at least three, at least four, at least five, at least six, or at least seven peaks) selected from peaks with d values (Å) comprise about 11.8; 5.9; 5.0; 4.9; 4.8; 4.7; 4.42; 4.35; 4.1; 3.9; 3.70; and 3.58. In certain embodiments, the XRPD pattern comprises one or more peaks (e.g., at least three, at least four, at least five, at least six, or at least seven peaks) selected from peaks with d values (Å) comprise about 11.8; 7.1; 6.1; 5.9; 5.1; 5.0; 4.9; 4.8; 4.7; 4.42; 4.35; 4.1; 4.1; 3.9; 3.9; 3.7; 3.6; 3.3; and 3.0. In some embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 18.1, 20.1, 20.4, 22.6, and 24.0. In some embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 18.1, 19.1, 20.1, 20.4, 21.5, 22.6, and 24.0. In some embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 17.8, 18.1, 18.5, 19.1, 20.1, 20.4, 21.5, 22.6, 24.0, and 24.8. In some embodiments, the crystalline tosylate salt has an XRPD pattern comprising one or more peaks (e.g., at least three, at least four, at least five, at least six, or at least seven peaks) selected from peaks with 2θ angle degrees of about 7.5, 12.5, 14.4, 15.1, 17.4, 17.8, 18.1, 18.5, 19.1, 20.1, 20.4, 21.5, 21.8, 22.6, 23.1, 24.0, 24.8, 26.9, and 29.8.

In certain embodiments, the crystalline tosylate salt comprises XRPD peaks at 2θ angle degrees or d values (Å) as provided in Table 9. In some embodiments, the crystalline tosylate salt has an XRPD pattern comprising one or more peaks (e.g., at least three, at least four, at least five, at least six, or at least seven peaks) selected from peaks with 2θ angle degrees of about 7.42, 15.01, 17.70, 18.01, 18.47, 18.98, 19.98, 20.33, 21.41, 22.58, 23.95, and 24.76. In some embodiments, the crystalline tosylate salt has an XRPD pattern comprising one or more peaks (e.g., at least three, at least four, at least five, at least six, or at least seven peaks) selected from peaks with 2θ angle degrees of about 7.42, 15.01, 18.01, 19.98, 20.33, 22.58, and 23.95. In some embodiments, the crystalline tosylate salt has an XRPD pattern comprising one or more peaks (e.g., at least three, at least four, at least five, at least six, or at least seven peaks) selected from peaks with 2θ angle degrees of about 7.42, 15.01, 17.70, 18.01, 19.98, 20.33, 21.41, 22.58, 23.95, and 24.76. In some embodiments, the crystalline tosylate salt has an XRPD pattern comprising one or more peaks (e.g., at least three, at least four, at least five, at least six, or at least seven peaks) selected from peaks with d values (Å) of about 11.90, 5.90, 5.01, 4.92, 4.44, 4.37, 4.15, 3.93, 3.71, and 3.59. In some embodiments, the crystalline tosylate salt has an XRPD pattern comprising one or more peaks (e.g., at least three, at least four, at least five, at least six, or at least seven peaks) selected from peaks with d values (Å) of about 11.90, 5.90, 5.01, 4.92, 4.80, 4.67, 4.44, 4.37, 4.15, 3.93, 3.71, and 3.59. In some embodiments, the crystalline tosylate salt has an XRPD pattern comprising one or more peaks (e.g., at least three, at least four, at least five, at least six, or at least seven peaks) selected from peaks with d values (Å) of about 11.90, 5.90, 4.92, 4.44, 4.37, 3.93, and 3.71.

In certain embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 9. In some embodiments, the crystalline tosylate salt has an XRPD pattern comprising one or more peaks (e.g., at least three, at least four, at least five, at least six, or at least seven peaks) selected from peaks with 2θ angle degrees of about 7.4, 15.0, 17.7, 18.0, 18.5, 19.0, 20.0, 20.3, 21.4, 22.6, 24.0, and 24.8. In some embodiments, the crystalline tosylate salt has an XRPD pattern comprising one or more peaks (e.g., at least three, at least four, at least five, at least six, or at least seven peaks) selected from peaks with 2θ angle degrees of about 7.4, 15.0, 18.0, 20.0, 20.3, 22.6, and 24.0. In some embodiments, the crystalline tosylate salt has an XRPD pattern comprising one or more peaks (e.g., at least three, at least four, at least five, at least six, or at least seven peaks) selected from peaks with 2θ angle degrees of about 7.4; 15.0; 17.7; 18.0; 20.0; 20.3; 21.4; 22.6; 24.0; and 24.8. In some embodiments, the crystalline tosylate salt has an XRPD pattern comprising one or more peaks (e.g., at least three, at least four, at least five, at least six, or at least seven peaks) selected from peaks with d values (Å) of about 11.9, 5.9, 5.0, 4.9, 4.44, 4.37, 4.1, 3.9, 3.7, and 3.6. In some embodiments, the crystalline tosylate salt has an XRPD pattern comprising one or more peaks (e.g., at least three, at least four, at least five, at least six, or at least seven peaks) selected from peaks with d values (Å) of about 11.9, 5.9, 5.0, 4.9, 4.8, 4.7, 4.44, 4.37, 4.1, 3.9, 3.7, and 3.6. In some embodiments, the crystalline tosylate salt comprises XRPD peaks at d values (Å) of about 11.9, 5.9, 4.9, 4.44, 4.37, 3.9, and 3.7.

In other embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 11. In other embodiments, the crystalline tosylate salt has an XRPD pattern comprising one or more peaks (e.g., at least three, at least four, at least five, at least six, or at least seven peaks) selected from peaks with 2θ angle degrees of about 7.42, 15.02, 17.38, 17.74, 18.03, 18.54, 19.02, 20.08, 20.39, 21.44, 22.63, 24.00, and 24.83. In other embodiments, the crystalline tosylate salt has an XRPD pattern comprising one or more peaks (e.g., at least three, at least four, at least five, at least six, or at least seven peaks) selected from peaks with 2θ angle degrees of about 7.42, 15.02, 18.03, 20.08, 20.39, 22.63, and 24.00. In other embodiments, the crystalline tosylate salt has an XRPD pattern comprising one or more peaks (e.g., at least three, at least four, at least five, at least six, or at least seven peaks) selected from peaks with d values (Å) of about 11.91, 5.89, 5.10, 5.00, 4.92, 4.78, 4.66, 4.42, 4.35, 4.14, 3.93, 3.71, and 3.58. In other embodiments, the crystalline tosylate salt has an XRPD pattern comprising one or more peaks (e.g., at least three, at least four, at least five, at least six, or at least seven peaks) selected from peaks with d values (Å) of about 11.91, 5.89, 4.92, 4.42, 4.35, 3.93, and 3.71.

In other embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 11. In other embodiments, the crystalline tosylate salt has an XRPD pattern comprising one or more peaks (e.g., at least three, at least four, at least five, at least six, or at least seven peaks) selected from peaks with 2θ angle degrees of about 7.4, 15.0, 17.3, 17.7, 18.0, 18.5, 19.0, 20.1, 20.4, 21.4, 22.6, 24.0, and 24.8. In other embodiments, the crystalline tosylate salt has an XRPD pattern comprising one or more peaks (e.g., at least three, at least four, at least five, at least six, or at least seven peaks) selected from peaks with 2θ angle degrees of about 7.4, 15.0, 18.0, 20.1, 20.4, 22.6, and 24.0. In other embodiments, the crystalline tosylate salt has an XRPD pattern comprising one or more peaks (e.g., at least three, at least four, at least five, at least six, or at least seven peaks) selected from peaks with d values (Å) of about 11.9, 5.9, 5.1, 5.0, 4.9, 4.8, 4.7, 4.42, 4.35, 4.1, 3.9, 3.7, and 3.6. In other embodiments, the crystalline tosylate salt has an XRPD pattern comprising one or more peaks (e.g., at least three, at least four, at least five, at least six, or at least seven peaks) selected from peaks with d values (Å) of about 11.9, 5.9, 4.9, 4.42, 4.35, 3.9, and 3.7.

In some embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 13. In other embodiments, the crystalline tosylate salt has an XRPD pattern comprising one or more peaks (e.g., at least three, at least four, at least five, at least six, or at least seven peaks) selected from peaks with 2θ angle degrees of about 7.46, 12.47, 14.45, 15.09, 17.40, 17.74, 18.11, 18.53, 19.05, 20.09, 20.43, 21.46, 22.63, 23.10, 24.03, 24.85, and 26.96. In other embodiments, the crystalline tosylate salt has an XRPD pattern comprising one or more peaks (e.g., at least three, at least four, at least five, at least six, or at least seven peaks) selected from peaks with 2θ angle degrees of about 7.46, 14.45, 15.09, 17.74, 18.11, 18.53, 19.05, 20.09, 20.43, 21.46, 22.63, 24.03, 24.85, and 26.96. In other embodiments, the crystalline tosylate salt has an XRPD pattern comprising one or more peaks (e.g., at least three, at least four, at least five, at least six, or at least seven peaks) selected from peaks with 2θ angle degrees of about 7.46, 15.09, 18.11, 20.09, 20.43, 22.63, and 24.03. In other embodiments, the crystalline tosylate salt has an XRPD pattern comprising one or more peaks (e.g., at least three, at least four, at least five, at least six, or at least seven peaks) selected from peaks with d values (Å) of about 11.84, 7.09, 6.13, 5.87, 5.09, 5.00, 4.89, 4.78, 4.66, 4.42, 4.34, 4.13, 4.08, 3.93, 3.85, 3.70, 3.58, 3.30, 2.99, and 2.86. In other embodiments, the crystalline tosylate salt has an XRPD pattern comprising one or more peaks (e.g., at least three, at least four, at least five, at least six, or at least seven peaks) selected from peaks with d values (Å) of about 11.84, 6.13, 5.87, 5.09, 5.00, 4.89, 4.78, 4.42, 4.34, 4.13, 3.93, 3.70, 3.58, and 3.30. In other embodiments, the crystalline tosylate salt has an XRPD pattern comprising one or more peaks (e.g., at least three, at least four, at least five, at least six, or at least seven peaks) selected from peaks with d values (Å) of about 11.84, 5.87, 4.89, 4.42, 4.34, 3.93, and 3.70.

In some embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 13. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 12.5, 14.5, 15.1, 17.4, 17.7, 18.1, 18.5, 19.0, 20.1, 20.4, 21.5, 22.6, 23.1, 24.0, 24.9, and 27.0. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 14.5, 15.1, 17.7, 18.1, 18.5, 19.0, 20.1, 20.4, 21.5, 22.6, 24.0, 24.9, and 27.0. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 18.1, 20.1, 20.4, 22.6, and 24.0. In other embodiments, the crystalline tosylate salt has an XRPD pattern comprising one or more peaks (e.g., at least three, at least four, at least five, at least six, or at least seven peaks) selected from peaks with d values (Å) of about 11.8, 7.1, 6.1, 5.9, 5.1, 5.0, 4.9, 4.8, 4.7, 4.4, 4.3, 4.13, 4.08, 3.9, 3.8, 3.7, 3.6, 3.3, 3.0, and 2.9. In other embodiments, the crystalline tosylate salt has an XRPD pattern comprising one or more peaks (e.g., at least three, at least four, at least five, at least six, or at least seven peaks) selected from peaks with d values (Å) of about 11.8, 6.1, 5.9, 5.0, 4.9, 4.8, 4.7, 4.4, 4.3, 4.1, 3.9, 3.7, 3.6, and 3.3. In other embodiments, the crystalline tosylate salt has an XRPD pattern comprising one or more peaks (e.g., at least three, at least four, at least five, at least six, or at least seven peaks) selected from peaks with d values (Å) of about 11.8, 5.9, 4.9, 4.4, 4.3, 3.9, and 3.7.

In some embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 17. In other embodiments, the crystalline tosylate salt has an XRPD pattern comprising one or more peaks (e.g., at least three, at least four, at least five, at least six, or at least seven peaks) selected from peaks with 2θ angle degrees of about 7.50, 12.51, 14.48, 15.12, 17.38, 17.78, 18.17, 18.58, 19.11, 20.09, 20.54, 21.54, 21.86, 22.65, 23.19, 24.08, 24.86, 26.98, 29.97, 30.44, 30.84, 32.07, 32.49, and 37.56. In other embodiments, the crystalline tosylate salt has an XRPD pattern comprising one or more peaks (e.g., at least three, at least four, at least five, at least six, or at least seven peaks) selected from peaks with 2θ angle degrees of about 7.50, 15.12, 17.38, 17.78, 18.17, 18.58, 19.11, 20.09, 20.54, 21.54, 21.86, 22.65, 23.19, 24.08, 24.86, and 26.98. In other embodiments, the crystalline tosylate salt has an XRPD pattern comprising one or more peaks (e.g., at least three, at least four, at least five, at least six, or at least seven peaks) selected from peaks with 2θ angle degrees of about 7.50, 15.12, 18.17, 20.09, 20.54, 22.65, and 24.08. In other embodiments, the crystalline tosylate salt has an XRPD pattern comprising one or more peaks (e.g., at least three, at least four, at least five, at least six, or at least seven peaks) selected from peaks with d values (Å) of about 11.78, 7.07, 6.11, 5.85, 5.10, 4.98, 4.88, 4.77, 4.64, 4.42, 4.32, 4.12, 4.06, 3.92, 3.83, 3.69, 3.57, 3.30, 2.98, 2.93, 2.78, 2.75, 2.39. In other embodiments, the crystalline tosylate salt has an XRPD pattern comprising one or more peaks (e.g., at least three, at least four, at least five, at least six, or at least seven peaks) selected from peaks with d values (Å) of about 11.78, 5.85, 5.10, 4.98, 4.88, 4.77, 4.64, 4.42, 4.32, 4.12, 4.06, 3.92, 3.83, 3.69, 3.57, and 3.30. In other embodiments, the crystalline tosylate salt has an XRPD pattern comprising one or more peaks (e.g., at least three, at least four, at least five, at least six, or at least seven peaks) selected from peaks with d values (Å) of about 11.78, 5.85, 4.88, 4.42, 4.32, 3.92, and 3.69.

In some embodiments, the crystalline tosylate salt has an XRPD pattern comprising one or more peaks (e.g., at least three, at least four, at least five, at least six, or at least seven peaks) selected from peaks with 2θ angle degrees or d values (Å) as provided in Table 17. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 12.5, 14.5, 15.1, 17.4, 17.8, 18.2, 18.6, 19.1, 20.1, 20.5, 21.5, 21.9, 22.6, 23.2, 24.1, 24.9, 27.0, 30.0, 30.4, 30.8, 32.1, 32.5, and 37.6. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 17.4, 17.8, 18.2, 18.6, 19.1, 20.1, 20.5, 21.5, 21.9, 22.6, 23.2, 24.1, 24.9, and 27.0. In other embodiments, the crystalline tosylate salt has an XRPD pattern comprising one or more peaks (e.g., at least three, at least four, at least five, at least six, or at least seven peaks) selected from peaks with 2θ angle degrees of about 7.5, 15.1, 18.2, 20.1, 20.5, 22.6, and 24.1. In other embodiments, the crystalline tosylate salt has an XRPD pattern comprising one or more peaks (e.g., at least three, at least four, at least five, at least six, or at least seven peaks) selected from peaks with d values (Å) of about 11.8, 7.1, 6.1, 5.9, 5.1, 5.0, 4.9, 4.8, 4.6, 4.4, 4.3, 4.12, 4.06, 3.9, 3.8, 3.7, 3.6, 3.3, 3.0, 2.9, 2.78, 2.75, 2.4. In other embodiments, the crystalline tosylate salt has an XRPD pattern comprising one or more peaks (e.g., at least three, at least four, at least five, at least six, or at least seven peaks) selected from peaks with d values (Å) of about 11.8, 5.9, 5.1, 5.0, 4.9, 4.8, 4.6, 4.4, 4.3, 4.12, 4.06, 3.9, 3.8, 3.7, 3.6, and 3.3. In other embodiments, the crystalline tosylate salt has an XRPD pattern comprising one or more peaks (e.g., at least three, at least four, at least five, at least six, or at least seven peaks) selected from peaks with d values (Å) of about 11.8, 5.9, 4.9, 4.4, 4.3, 3.9, and 3.7.

In some embodiments, the crystalline tosylate salt has an XRPD pattern substantially as provided in FIG. 6. In some embodiments, the crystalline tosylate salt has an XRPD pattern comprising one or more peaks (e.g., at least three, at least four, at least five, at least six, or at least seven peaks) selected from peaks with 2θ angle degrees as provided in Table 25. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.51, 14.47, 15.14, 17.41, 18.12, 18.53, 19.07, 20.09, 20.46, 21.48, 21.81, 24.05, 24.83, and 29.81. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.51, 14.47, 15.14, 20.09, 21.48, and 24.05. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.51, 15.14, 18.12, 20.09, 20.46, 22.65, and 24.05. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.51, 20.09, and 24.05. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.5, 14.5, 15.1, 17.4, 18.1, 18.5, 19.1, 20.1, 20.46, 21.48, 21.8, 24.1, 24.8, and 29.8. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.5, 14.5, 15.1, 20.1, 21.5, and 24.1. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.5, 15.1, 18.1, 20.1, 20.5, 22.6, and 24.1. In some embodiments, the crystalline tosylate salt has an XRPD pattern comprising one or more peaks (e.g., at least three, at least four, at least five, at least six, or at least seven peaks) selected from peaks with ±about 0.2 2θ angle degrees of about 7.5, 20.1, and 24.1. In some embodiments, the crystalline tosylate salt has an XRPD pattern comprising one or more peaks (e.g., at least three, at least four, at least five, at least six, or at least seven peaks) selected from peaks with d values (Å) as provided in Table 25. In other embodiments, the crystalline tosylate salt has an XRPD pattern comprising one or more peaks (e.g., at least three, at least four, at least five, at least six, or at least seven peaks) selected from peaks with d values (Å) of about 11.8, 6.1, 5.9, 5.1, 4.9, 4.8, 4.6, 4.4, 4.3, 4.1, 4.1, 3.7, 3.6, and 3.0. In other embodiments, the crystalline tosylate salt has an XRPD pattern comprising one or more peaks (e.g., at least three, at least four, at least five, at least six, or at least seven peaks) selected from peaks with d values (Å) of about 11.8, 6.1, 5.9, 4.4, 4.1, and 3.7. In other embodiments, the crystalline tosylate salt has an XRPD pattern comprising one or more peaks (e.g., at least three, at least four, at least five, at least six, or at least seven peaks) selected from peaks with d values (Å) of about 11.8, 5.9, 4.9, 4.4, 4.3, 3.9, and 3.7. In other embodiments, the crystalline tosylate salt has an XRPD pattern comprising one or more peaks (e.g., at least three, at least four, at least five, at least six, or at least seven peaks) selected from peaks with d values (Å) of about 11.8, 4.4, and 3.7.

In some or any embodiments, the crystalline tosylate salt exhibits a $^{13}C$ NMR spectrum corresponding substantially to the spectrum in FIG. 12 or exhibits a spectrum with peaks corresponding substantially to those in Table 28. In some or any embodiments, the crystalline tosylate salt exhibits a $^{13}C$ NMR spectrum with one or more peaks (e.g., at least three, at least four, at least five, at least six, or at least seven peaks) selected from about ±0.2 ppm at about 166.9, 164.3, 162.2, 160.6, 151.8, 149.4, 143.2, 140.2, 139.1, 136.0, 131.8, 129.4, 128.6, 127.7, 123.9, 116.8, 115.1, 112.2, 105.2, 100.3, 58.5, 45.3, 37.4, and 23.9. In some or any embodiments, the crystalline tosylate salt exhibits a $^{13}C$ NMR spectrum with peaks about +0.2 ppm at about 151.8, 149.4, 143.2, 136.0, 131.8, 123.9, 116.8, 115.1, 112.2, 105.2, 100.3, 58.5, 45.3, 37.4, and 23.9. In some or any embodiments, the crystalline tosylate salt exhibits a $^{13}C$ NMR spectrum with peaks about +0.2 ppm at about 143.2, 136.0, 131.8, 123.9, 112.2, 105.2, 100.3, 58.5, 45.3, 37.4, and 23.9. In some or any embodiments, the crystalline tosylate salt exhibits a $^{13}C$ NMR spectrum with peaks about ±0.2 ppm at about 143.2, 136.0, 131.8, 123.9, 112.2, 105.2, and 100.3.

In some or any embodiments, the crystalline salt has an XRPD peaks at 2θ angle degrees of about 7.4, 15.1, 17.4, 17.8, 18.1, 18.5, 19.1, 20.1, 20.4, 21.5, 22.6, 24.0, 24.8, and 27.0. In some or any embodiments, the crystalline salt has an XRPD peaks at 2θ angle degrees of about 7.4, 15.1, 18.1, 19.1, 20.1, 20.4, 21.5, 22.6, and 24.0. In some or any embodiments, the crystalline salt has an XRPD peaks at 2θ angle degrees of about 7.4, 15.1, 20.1, 20.4, 22.6, 24.0, and 24.8. In some or any embodiments, the crystalline salt has an XRPD peaks at 2θ angle degrees of about 7.4, 15.1, 18.1, 20.1, 20.4, 22.6, and 24.0.

In some or any embodiments, the crystalline salt has an XRPD pattern comprising peaks at d values (Å) of about 11.9, 5.9, 5.1, 5.0, 4.9, 4.8, 4.6, 4.4, 4.3, 4.1, 3.9, 3.7, 3.6, and 3.3. In some or any embodiments, the crystalline salt has an XRPD pattern comprising peaks at d values (Å) of about 11.9, 5.9, 4.9, 4.6, 4.4, 4.3, 4.1, 3.9, and 3.7. In some or any embodiments, the crystalline salt has an XRPD pattern comprising peaks at d values (Å) of about 11.9, 5.9, 4.4, 4.3, 3.9, 3.7, and 3.6. In some or any embodiments, the crystalline salt has an XRPD peaks at d values (Å) of about 11.9, 5.9, 4.9, 4.4, 4.3, 3.9, and 3.7.

In some or any embodiments, crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate is a crystalline polymorph exhibiting at least one of a solid state $^{13}$C NMR spectrum with peaks at 143.2, 136.0, 131.8, 123.9, 112.2, 105.2, and 100.3 ppm±0.2 ppm;

an X-ray diffraction pattern comprising characteristic peaks expressed in d-values (Å): 11.9, 5.9, 4.9, 4.4, 4.3, 3.9, and 3.7; and an X-ray diffraction pattern comprising peak reflectances at 2θ angle degrees±0.2 2θ angle degrees of 7.4, 15.1, 18.1, 20.1, 20.4, 22.6, and 24.0.

In some embodiments, the crystalline tosylate salt exhibits a single endothermal peak on differential scanning calorimetry between room temperature and about 350° C., where the single endothermal peak maximum occurs between about 320° C. to about 335° C. In certain embodiments, the single endothermal peak maximum occurs at between about 330° C. to about 335° C. In some embodiments, the single endothermal peak maximum occurs at about 333° C. to about 334° C.

In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has no observable endotherm from about 25° C. to about 250° C. as determined by DSC. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has a DSC thermogram comprising an endotherm with a maximum at between about 320° C. to about 335° C., between 330° C. to about 335° C., or between about 333° C. to about 334° C. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has a DSC thermogram corresponding substantially to the DSC thermograph of FIG. 2a, 3a, 4a, 5a, or 7a.

In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has a DVS isotherm plot corresponding substantially to the DVS isotherm plot of FIG. 9. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein does not exhibit significant weight change (e.g., less than about 0.05 wt %, less than about 0.1 wt %, less than about 0.15 wt %, or less than about 0.2 wt %) from about 0% to about 95% relative humidity.

In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has a TGA thermogram corresponding substantially to the TGA thermograph of FIG. 2b, 3b, 4b, 5b, or 7b. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein has a TGA thermogram that does not exhibit significant weight loss (e.g., less than about 0.05 wt %, less than about 0.1 wt %, less than about 0.5 wt %, less than about 1 wt %, less than about 5 wt %, less than about 10 wt %, less than about 15 wt %, less than about 20 wt %, or less than about 25 wt %) when heated from about room temperature to a temperature of about 200° C., about 210° C., about 220° C., about 230° C., about 240° C., about 250° C., about 260° C., about 270° C., about 280° C., about 290° C., about 300° C., about 310° C., about 320° C., or greater than about 320° C. In various embodiments, the crystalline tosylate salt provided herein has a weight loss of no greater than about 1%, no greater than about 0.5%, or no greater than about 0.1% in a thermogravimetric thermogram between about 25° C. to about 200° C.

In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein is unsolvated. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein is anhydrous. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein is thermally stable. In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein is non-hygroscopic.

In certain embodiments, a crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one as provided herein exhibits desirable characteristics for the preparation, processing and/or storage of a pharmaceutical composition or drug product comprising the crystalline tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one.

In another aspect, a method of synthesizing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is provided. Scheme A provides an exemplary outline of the synthetic method. In its various embodiments, the method comprises 3 steps, the first of which is contacting methyl 5-fluoro-2-(2-(1-methyl-1H-1,2,4-triazol-5-yl)acetyl)-3-nitrobenzoate, that is,

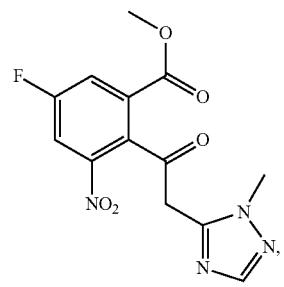 [SMILES: COC(=O)c1cc(F)cc([N+](=O)[O-])c1C(=O)Cc1ncnn1C]

with 4-fluorobenzaldehyde in a mixture comprising one or more step (a) solvent(s) and titanium(III) chloride to make a first intermediate (b in Scheme A). In certain embodiments, the one or more step (a) solvent(s) are selected from THF and MeOH, for example, in volume to volume ratio of 6 parts THF to 1 part MeOH. Titanium (III) chloride can be added to the first reaction mixture at 0° C. to room temperature.

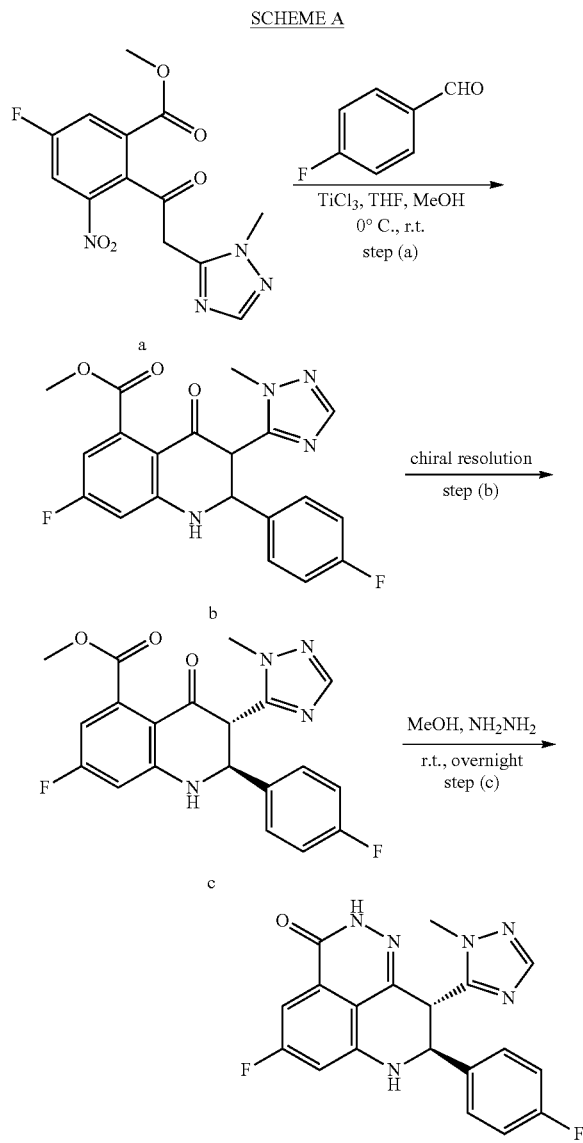

In some embodiments, the reaction mixture comprising methyl 5-fluoro-2-(2-(1-methyl-1H-1,2,4-triazol-5-yl)acetyl)-3-nitrobenzoate, one or more step (a) solvent(s), and titanium (III) chloride is stirred at a temperature of about 30° C. to about 50° C.

The second step (step (b)) of the synthetic method provided is isolating by chiral separation an enantiomer (c) of the first intermediate (b). Chiral resolution of the first intermediate (b) into its enantiomers may be performed by any method known to those skilled in the art, for example, by chromatographic methods such as high performance liquid chromatography and supercritical fluid chromatography. The enantiomer shown as c in Scheme A can be isolated in the second step of the synthetic method.

The third step (step (c)) of the synthetic method comprises contacting the isolated enantiomer (c) of the first intermediate (b) with one or more step (c) solvent(s) and hydrazine monohydrate to make (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In certain embodiments, the one or more step (c) solvent(s) is independently selected from methanol, ethanol, and acetonitrile. In certain embodiments, the step (c) solvent is methanol. In certain embodiments, the step (c) solvent is ethanol. In other embodiments, the step (c) solvent is acetonitrile. Typically, the third step can be carried out at room temperature allowing the reaction to go overnight.

Alternatively, intermediate b is treated with a solvent, such as methanol, ethanol, or acetonitrile, and hydrazine monohydrate to make 5-fluoro-8-(4-fluorophenyl)-9-(1-methyl-1H-1,2,4-triazol-5-yl)-8,9-dihydro-2H-pyrido[4,3,2-de]phthalazin-3(7H)-one which is then resolved by chiral resolution into (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. Chiral resolution may be performed by any method known to those skilled in the art, for example, by chromatographic methods such as high performance liquid chromatography, supercritical fluid chromatography, and simulating moving bed chromatography.

In another aspect, a method of preparing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one tosylate salt is provided. The method of preparing the tosylate salt provided herein is amenable to large scale production of the tosylate salt and can fulfill GMP requirements.

In certain embodiments, the preparative method comprises contacting free base of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one in one or more solvent(s) with p-toluenesulfonic acid and removing the one or more solvent(s) to make (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt. In certain embodiments, the free base is obtained according to the methods described herein for synthesizing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one.

In some or any embodiments of the preparative method for the tosylate salt form, the free base is suspended or dissolved in one or more solvents independently selected from THF, acetone, methanol, acetonitrile, and DCM. In certain embodiments of the preparative method for the tosylate salt form, the free base is suspended or dissolved in a mixture of methanol and acetonitrile. In certain embodiments of the preparative method for the tosylate salt form, the free base is suspended or dissolved in a mixture of DCM and acetonitrile. In certain embodiments of the preparative method for the tosylate salt form, the free base is suspended or dissolved in a mixture of acetone and THF. In certain embodiments of the preparative method for the tosylate salt form, the free base is suspended or dissolved in acetone. In certain embodiments of the preparative method for the tosylate salt form, the free base is suspended or dissolved in THF. In certain embodiments of the preparative method for the tosylate salt form, the free base is suspended or dissolved in one or more solvents independently selected from THF, acetone, methanol, acetonitrile, and DCM, and heated prior to adding TsOH. In certain embodiments of the preparative method for the tosylate salt form, the free base is suspended or dissolved in a mixture of acetone and THF, and heated prior to adding TsOH. In some embodiments, the free base is suspended in a solvent consisting essentially of THF. In certain embodiments of the preparative method for the tosylate salt form, the free base is suspended or dissolved in THF and heated prior to adding TsOH.

In some or any embodiments, p-toluenesulfonic acid is dissolved or suspended in one or more solvents and is then added to the free base which is suspended or dissolved in a second set of one or more solvents. In some or any embodiments, the free base is dissolved or suspended in one or more solvents and is then added to the p-toluenesulfonic acid which is suspended or dissolved in a second set of one or more solvents.

In some or any embodiments, (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is contacted with p-toluenesulfonic acid at an elevated temperature. In some or any embodiments, TsOH and the free base can be contacted at a temperature of between about 0° C. to about 70° C. Typically, the free base has a temperature of about 20° C. to 55° C. when contacted with the TsOH. In some or any embodiments, the free base is contacted with TsOH when the temperature is about 30° C. to about 70° C., about 25° C. to about 30° C., about 30° C. to about 40° C., about 40° C. to about 50° C., about 50° C. to about 60° C., about 60° C. to about 70° C., or about 48° C. to about 58° C. The solvent can be removed and the salt dried according to methods known to those skilled in the art.

In some or any embodiments, after the free base is contacted with the TsOH, the resulting solution/suspension is allowed to stand under conditions sufficient to precipitate a crystalline form and the crystalline form is isolated. In some or any embodiments, the conditions sufficient to precipitate the crystalline form include cooling. In some or any embodiments, the conditions sufficient to precipitate the crystalline form include cooling to 25° C. or cooler.

In addition to the methods provided herein, solid forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one provided herein can also be prepared using techniques known in the art, including, but not limited to, melt cooling, rapid melt cooling, freeze drying, spray drying, roller drying, lyophilization, quench cooling the melt, rapid solvent evaporation, slow solvent evaporation, solvent recrystallization, slurry recrystallization, melt crystallization, desolvation, sublimation, recrystallization in confined spaces (e.g., in nanopores or capillaries), recrystallization on surfaces or templates (e.g., on polymers), recrystallization in the presence of additives (e.g., co-crystal counter-molecules), dehydration, rapid cooling, slow cooling, vapor diffusion, grinding, cryo-grinding, solvent-drop grinding, microwave-induced precipitation, ultrasonication-induced precipitation, laser-induced precipitation, and precipitation from a supercritical fluid.

Another aspect is a method of preparing (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7M-one tosylate salt comprising step (1): in the presence of one or more step 1 solvent(s) independently selected from THF, acetone, methanol, acetonitrile, and DCM, contacting (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one with p-toluenesulfonic acid at an elevated temperature;

step (2): allowing to stand under conditions sufficient to precipitate the crystalline form; and step (3): isolating the crystalline form.

In some or any embodiments, the elevated temperature is about 30° C. to about 70° C. In some or any embodiments, the one or more step 1 solvent(s) are independently selected from methanol and acetonitrile. In some or any embodiments, the one or more step 1 solvent(s) are independently selected from DCM and acetonitrile. In some or any embodiments, the one or more step 1 solvent(s) are independently selected from acetone and THF. In some or any embodiments, the step 1 solvent is acetone. In some or any embodiments, the step 1 solvent is THF. In some or any embodiments, the conditions sufficient to precipitate the crystalline form include cooling. In some or any embodiments, the conditions sufficient to precipitate the crystalline form include cooling to 25° C. or cooler. In some or any embodiments, the method further comprises step (a): contacting

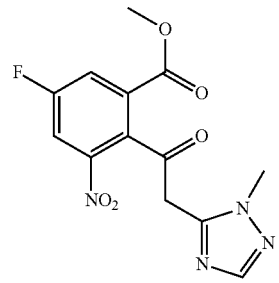 [SMILES: COC(=O)c1cc(F)cc([N+](=O)[O-])c1C(=O)Cc1ncnn1C]

with 4 fluorobenzaldehyde in a mixture comprising one or more step (a) solvent(s) and titanium(III) chloride to make a first intermediate;

step (b): isolating by chiral separation an enantiomer of the first intermediate; and step (c): contacting the isolated enantiomer of the first intermediate with hydrazine monohydrate in one or more step (c) solvent(s) to make (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In some or any embodiments, the isolated enantiomer of the first intermediate is contacted with hydrazine monohydrate in one or more step (c) solvent(s) independently selected from methanol, ethanol, and acetonitrile. In some or any embodiments, the one or more step (a) solvent(s) are independently selected from THF and methanol. In some or any embodiments, the method further comprises step (x): contacting

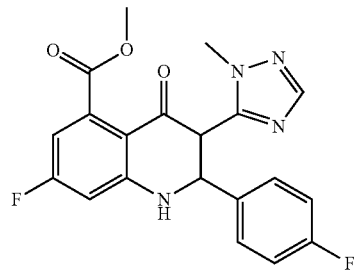 [SMILES: COC(=O)c1cc(F)cc2c1C(=O)C(c1ncnn1C)C(c1ccc(F)cc1)N2]

with hydrazine monohydrate in one or more step x solvents to yield 5-fluoro-8-(4-fluorophenyl)-9-(1-methyl-1H-1,2,4-triazol-5-yl)-8,9-dihydro-2H-pyrido[4,3,2-de]phthalazin-3(7H)-one; and step (y): isolating (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one by chiral separation. In some or any embodiments, the one or more step (x) solvent(s) is independently selected from methanol, ethanol, and acetonitrile.

In certain embodiments, a (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt prepared according to methods described in the preceding paragraphs, or as substantially described in the following examples, is provided. For instance, in some embodiments, a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one crystallized from a solvent consisting essentially of tetrahydrofuran (THF) is provided.

In some or any embodiments, the tosylate salt exhibits less than 2% thermal weight loss at or below a temperature of about 280° C. by TGA.

In some or any embodiments, the tosylate salt exhibits a value of hystersis less than about 1% in DVS at 25° C. from RH0 % to RH95%.

Compositions, Including Pharmaceutical Compositions

In yet another aspect, compositions are provided that comprise or consist essentially of substantially pure (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt, in another embodiment in a crystalline form thereof as provided herein.

In some embodiments, a pharmaceutical composition is provided comprising a tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, including a crystalline form thereof as described herein, and a pharmaceutically acceptable excipient and/or carrier. The choice of excipient, to a large extent, depends on factors, such as the particular mode of administration, the effect of the excipient on the solubility and stability of the active ingredient, and the nature of the dosage form.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt sufficient to produce a desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

Amounts of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in unit dosage forms can, for example, be from about 5 µg to about 1500 µg, from about 20 µg to about 1250 µg, from about 25 µg to about 1000 µg, or from about 25 µg to about 250 µg. In some embodiments, the amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in a unit dosage form comprises (where the following do not including mass contributed by the tosylate portion of the salt) about 5 µg to about 30 µg, from about 20 µg to about 60 µg, from about 50 µg to about 100 µg, from about 120 µg to about 250 µg, from about 20 µg to about 112 µg, or from about 25 µg to about 250 µg (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. In certain embodiments, the amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one is about 10 µg, about 20 µg, about 25 µg, about 30 µg, about 50 µg, about 75 µg, about 100 µg, about 150 µg, about 200 µg, about 250 µg, or about 1000 µg.

Oral Dosage Forms. In certain embodiment, the pharmaceutical composition, as provided herein, is formulated for oral administration to a subject. Pharmaceutical compositions suitable for oral administration can be presented as discrete dosage forms, such as, but are not limited to, tablets, chewable tablets, caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

For instance, oral dosage forms provided herein may be prepared by combining (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt, in one embodiment in a crystalline form thereof as provided herein (hereinafter, the "active ingredient"), an intimate admixture with at least one excipient according to conventional pharmaceutical compounding techniques. Excipients can take a wide variety of forms depending on the form of preparation desired for administration. Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredient with liquid carriers, finely divided solid carriers, or both, and then shaping the product into the desired presentation if necessary. Disintegrants or lubricants can be used in pharmaceutical compositions and dosage forms of the invention. Production of pharmaceutical compositions or dosage forms in accordance with the present invention may require, in addition to the therapeutic drug ingredients, excipients or additives including, but not limited to, diluents, binders, lubricants, disintegrants, colorants, flavors, sweetening agents and the like or mixtures thereof. By the incorporation of these and other additives, a variety of dosage forms (e.g., tablets, capsules, caplets, troches and the like) may be made. These include, for example, hard gelatin capsules, caplets, sugar-coated tablets, enteric-coated tablets (for example to delay action), multiple compressed tablets, prolonged-action tablets, tablets for solution, effervescent tablets, buccal and sublingual tablets, troches and the like. The dose form or dosage formulation may be formed by methods well known in the art. See, e.g., *Remington's Pharmaceutical Sciences,* 16th and 18th eds., Mack Publishing Co., Easton, Pa. (1980 and 1990). See also *U.S. Pharmacopeia XXI*, U.S. Pharmacopeia Convention, Inc., Rockville, Md. (1985).

Other Dosage Forms. In certain embodiments, the pharmaceutical composition as provided herein can be formulated in parenteral dosage forms. Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are in some embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms provided herein are well known to those skilled in the art.

In yet other embodiments, the pharmaceutical composition as provided herein can be formulated in a transdermal, topical or mucosal dosage form. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16$^{th}$ and 18$^{th}$ eds., Mack Publishing, Easton Pa. (1980 & 1990); and *Introduction to Pharmaceutical Dosage Forms,* 4$^{th}$ ed., Lea & Febiger, Philadelphia (1985). Suitable excipients (e.g., carriers and diluents) and other materials that can be used to provide transdermal, topical, and mucosal dosage forms encompassed by this disclosure are well known to those skilled in the pharmaceutical arts, and depend on the particular tissue to which a given pharmaceutical composition or dosage form will be applied.

Methods of Treatment

Provided herein are methods for the treatment of a disease or condition, or symptom thereof, as explained below.

In some or any embodiments, provided herein is a use of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt for the treatment of a disease or condition, or symptom thereof, in a subject.

In some or any embodiments, a method of treating a cancer, or symptom thereof, comprising administering to a subject with a cancer a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.

Some or any embodiments provide a method of potentiation of cytotoxic cancer therapy in a subject in recognized need of such treatment comprising administering to the subject a therapeutically acceptable amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.

In some or any embodiments, provided herein is a method for the treatment of a cancer, comprising administering to a subject in need of treatment a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in combination with ionizing radiation and/or one or more chemotherapeutic agents. In some or any embodiments, the compound described herein is administered simultaneously with ionizing radiation and/or one or more chemotherapeutic agents. In some or any embodiments, the compound described herein is administered sequentially with ionizing radiation and/or one or more chemotherapeutic agents. Ionizing radiation and chemotherapeutic agents are known to those skilled in the art.

In some or any embodiments, the therapeutic agent(s) is an alkylating agent, such as methyl methanesulfonate (MMS), temozolomide and dacarbazine (DTIC); a topoisomerase-1 inhibitor such as Topotecan, Irinotecan, Rubitecan, Exatecan, Lurtotecan, Gimetecan, Diflomotecan (homocamptothecins), 7-substituted non-silatecans, the 7-silyl camptothecins (BNP 1350), SN38, NK012 (a SN-38-releasing nanodevice constructed by covalently attaching SN-38 to the block copolymer PEG-PGlu, followed by self-assembly of amphiphilic block copolymers in aqueous media), and XR 11576/MLN 576; alemtuzumab; arsenic trioxide; asparaginase (pegylated or non-); bevacizumab; cetuximab; platinum-based compounds such as cisplatin, carboplatin, oxaliplatin, and triplatin tetranitrate; cladribine; daunorubicin; doxorubicin; idarubicin; fludarabine; 5-fluorouracil; gemtuzumab; methotrexate; Paclitaxel™; taxol; temozolomide; thioguanine; hormone therapies such as an antiestrogen, an antiandrogen, and gonadotropin releasing hormone analogues; interferons such as alpha interferon; nitrogen mustards such as busulfan, melphalan, and mechlorethamine; retinoids such as tretinoin; tyrosine kinase inhibitors such as gefinitinib and imatinib; a proteasome inhibitor such as bortezomib; or agents to treat signs or symptoms induced by such therapy including allopurinol, filgrastim, granisetron/ondansetron/palonosetron, and dronabinol.

In some or any embodiments, provided is a method for the treatment of a cancer, comprising administering to a subject in need of treatment a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in combination with a topoisomerase inhibitor. In some or any embodiments, the topoisomerase inhibitor is SN38, irinotecan, or NK012. In some or any embodiments, the topoisomerase inhibitor is irinotecan. In some or any embodiments, the cancer is breast cancer.

In some or any embodiments, provided is a method for the treatment of a cancer, comprising administering to a subject in need of treatment a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in combination with a platin. In some or any embodiments, the platin is cisplatin, carboplatin, oxaliplatin, or triplatin tetranitrate. In some or any embodiments, the topoisomerase inhibitor is cisplatin. In some or any embodiments, the cancer is breast cancer.

In some or any embodiments, provided is a method for the treatment of a cancer, comprising administering to a subject in need of treatment a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt in combination with temozolomide. In some or any embodiments, the cancer is colorectal cancer.

In some embodiments, provided herein is a method of treatment of a cancer deficient in Homologous Recombination (HR) dependent DNA double strand break (DSB) repair pathway, which includes administering to a subject in need of treatment a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt. In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2.

In certain embodiments, the cancer to be treated comprises phosphatase and tensin homolog (PTEN) deficient cells (e.g., cells in which PTEN is mutated or its expression is minimal or absent). In certain embodiments, the cancer to be treated comprises cells with a PTEN gene mutation. Exemplary cancers associated with PTEN deficiency can include, for example, glioblastoma, endometrial cancers, prostate cancer, lung cancer and breast cancer.

In certain embodiments, the cancer to be treated is one resulting from an activation mutation of the Wnt signaling pathway ("Wnt mediated cancers"). It will be understood that by "activation mutation of the Wnt signaling pathway" it is meant to include, for example, oncogene mutations in genes leading to accumulation of β-catenin in cancer cells, gain-offunction mutations in the CTNNB1 gene (which encodes (β-catenin), mutations in the APC tumor suppressor gene or mutations in the AXIN2 gene. It is believed, for instance, and without intending to be limited to any theory or mechanism, that useful treatment of a Wnt mediated cancer may be had by way of inhibiting tankyrase, an enzyme having poly(ADP-ribose) polymerase activity. Exemplary Wnt mediated cancers that can be treated according to the methods provided herein include, for instance, bladder cancer, breast fibromatoses, cervical cancer, colorectal cancer, colon carcinoma, Desmoid tumor, esophageal adenocarcinoma, familial adenomatous polyposis, fundic gland polyps, gastric carcinoma, gastric adenoma, gastrointestinal carcinoid tumor, hepatoblastoma, hepatocellular carcinoma, juvenile nasopharyngeal angiofibroma, non-Hodgkin lymphoma, lung adenocarcinoma, medulloblastoma, melanoma, ovarian carcinoma, pancreatic cancer (including, for example, non-ductal solid pseudopapillary and non-ductal acinal cell carcinoma), pancreoblastoma, pilomatricomas, prostate cancer, small intestinal adenocarcinoma, synovial sarcoma, thyroid carcinoma, uterine cervical cancer, uterine endometrial cancer and Wilm's tumor.

In some embodiments of the method of treatment of a cancer, or symptom thereof, provided herein, the cancer is bladder cancer, breast cancer (including metastatic, BRCA-positive, and BRCA-negative), cervical cancer, colon cancer, colorectal cancer, EBV-associated tumors (including Burkitt's lymphoma, nasopharyngeal carcinoma, lymphomas in AIDS patients, smooth muscle tumors in AIDS patients, Hodgkin's disease, non-Hodgkin's lymphoma, lymphoproliferative disease in immunosuppressed patients, leiomyosarcomas in immunosuppressed patients, EBV+ gastric cancer, EBV+ breast cancer, T-cell lymphoma), endometrial cancers (including carcinomas and sarcomas), gastrointestinal stromal tumor, gliomas, glioblastoma (including, for instance, glioblastoma multiforme and anaplastic astrocytoma), head and neck cancer, hepatocellular carcinoma, hereditary non-polyposis colon cancer (HNPCC), kidney cancer, leukemia (including acute myelogenous leukemia, chronic lymphocytic leukemia), lung cancer (including non small cell lung carcinoma, small cell lung carcinoma), lymphoma (including mantle cell lymphoma), medulloblastoma, melanoma, meningioma, myelodysplastic syndrome, ovarian cancer (including advanced, high grade serous, platinum-sensitive, platinum-resistant, platinum-refractory, and BRCA-negative), pancreatic cancer (including BRCA-negative), peritoneal cancer, prostate cancer (including BRCA-negative, metastatic, and castration resistant), renal cancer, thyroid cancer, uterine carcinosarcoma, or uterine cancer.

In certain embodiments, provided herein is a method of treating a disease or condition, or symptom thereof, associated with a PTEN deficiency comprising administering to a subject with the disease or condition associated with a PTEN deficiency a therapeutically-effective amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt. Exemplary diseases and conditions associated with a PTEN deficiency include, for example, Cowden syndrome, Bannayan-Riley-Ruvalcaba syndrome, Lhermitte-Duclos disease, Proteus syndrome, Proteus-like syndrome or hamartome tumor syndrome.

Certain embodiments provide a method of treating inflammatory diseases including, but not limited to, arthritis, gout, inflammatory bowel disease, CNS inflammation, multiple sclerosis, allergic encephalitis, sepsis, septic shock, hemorrhagic shock, pulmonary fibrosis, and uveitis in a subject in recognized need of such treatment comprising administering to the subject a therapeutically acceptable amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.

Certain embodiments provide a method of treating immunological diseases or disorders such as rheumatoid arthritis and septic shock in a subject in recognized need of such treatment comprising administering to the subject a therapeutically acceptable amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.

Certain embodiments provide a method of treating degenerative diseases including, but not limited to, diabetes and Parkinson's disease in a subject in recognized need of such treatment comprising administering to the subject a therapeutically acceptable amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.

In certain embodiments of this use, the precise amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt administered depends on the patient's state of health, weight, and the like. In some embodiments, it is considered appropriate for the caregiver to determine such therapeutically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain embodiments of the methods of treatment provided herein, including those provided above, the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt can be administered in a solid form. In some embodiments, the salt is administered in a crystalline form.

In certain embodiments of the methods of treatment provided herein, the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt is administered to the subject in a regimen of about 1 week, about 2 weeks, about 3 weeks, about 1 month, about 2 months or about 6 months. In some embodiments the tosylate salt is administered daily in the regimen. In other embodiments, the tosylate salt is administered for 2, 3 or 4 days per week, interspersed or followed by days of the weekly regimen where the tosylate salt is not administered.

In certain instances, a patient's condition does not improve or does not significantly improve following administration of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt, including in crystalline form, and, upon the doctor's discretion, the administration of the compound is optionally administered chronically, that is, for an extended period of time, including throughout the duration of the patient's life in order to ameliorate or otherwise control or limit the symptoms of the patient's disease or condition.

In certain cases where the patient's status does improve or does not substantially improve, upon the doctor's discretion the administration of the active ingredient is optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days.

In certain embodiments, the amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 5 to about 8000 µg per day, in a specific embodiment about 10 to about 5000 µg per day. In certain embodiments, the amount of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt to be administered is between about 50 µg to about 5000 µg, between about 50 µg to about 1500 µg, between about 50 µg to about 1000 µg, between about 50 µg to about 500 µg, between about 50 µg to about 250 µg, between about 50 µg to about 200 µg, between about 50 µg to about 150 µg, between about 50 µg to about 100 µg, between about 25 µg to about 2500 µg, between about 25 µg to about 1000 µg, between about 25 µg to about 250 µg, between about 25 µg to about 150 µg, or between about 25 µg to about 75 µg. In various embodiments, the desired dose is conveniently presented in a single dose or as divided doses administered simultaneously (or over a short period of time) or at appropriate intervals, for example as two, three, four or more sub-doses per day.

In certain embodiments, the daily dosages appropriate for the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt described herein are from about 0.1 to about 200 µg/kg body weight. In certain embodiments, the daily dosage is from about 0.3 to about 3.0 µg/kg body weight. In some embodiments, an indicated daily dosage in the larger subject, including, but not limited to, humans, is in the range from about of about 25 to about 8000 µg, conveniently administered in divided doses, including, but not limited to, up to four times a day or in extended release form. In certain embodiments, suitable unit dosage forms for oral administration comprise those described above. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

EXAMPLES

Methods and Procedures. Reagents and solvents used below can be obtained from commercial sources such as Aldrich Chemical Co. (Milwaukee, Wis., USA). Routine chemical analyses were conducted using NMR, MS and HPLC. Significant NMR peaks are tabulated by chemical shift and labeled with multiplicity (s, singlet; d, doublet; t, triplet; q, quartet; m, multiplet; br s, broad singlet) and number of protons. Mass spectrometry data is provided in relation to the mass of the parent ion, M. HPLC data is provided as a purity percentage.

Unless otherwise noted, The XRPD patterns were acquired on a Bruker D8 Advance diffractometer (Bruker AXS Inc., Madison, Wis., USA). Samples were gently flattened onto a zero-background silicon insert sample holder. A continuous 2θ scan range of 4° to 40° was used with a Cu Kα (λ 1.54056 Å) radiation source and a generator power of 40 kV and 40 mA. A 2θ step size of 0.05 degrees/step with a step time of 1 second/step was used. Experiments were performed at room temperature and at ambient humidity. Standard error was about 0.2 2θ angle degrees. The entire list of peaks identified in the XRPD pattern, or a subset thereof, may be sufficient to characterize the polymorph(s) obtained.

Unless otherwise noted, DSC thermograms were acquired using a TA Instruments Q2000 Differential Scanning calorimeter (New Castle, Del., USA). The sample was weighed out directly into an aluminum DSC pan. The pan was sealed by applying pressure by hand and pushing each part of the pan together (also known as a loose lid configuration). Except as noted below, the temperature was ramped from 25.00° C. to 400.00° C. at 10.00° C./minute. In the DSC figures, exothermic events are plotted in the upward direction.

Unless otherwise noted, TGA thermograms were acquired using a TA Instruments Q500 Thermogravimetric Analyzer (New Castle, Del., USA). Samples were weighed out into the pan. Except as noted below, the temperature was ramped from 25.00° C. to 400.00° C. at 10.00° C./minute.

Unless otherwise noted, DVS were acquired using standard procedures on a DVS ADVANTAGE 1 model from Surface Measurement Systems Ltd. (Alperton, Middlesex, UK). A moisture adsorption desorption isotherm was performed as outlined below. The standard isotherm run is a cycle starting at RH 0% to RH 95% at 5% intervals, followed by drying to RH 0% in 5% RH intervals.

Exemplary Synthesis of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one This example provides a representative process for the preparation of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one in accordance with one aspect of the disclosure. The synthesis is outlined in Scheme A.

Preparation of b. To a suspension of a (5 g, 15.5 mmol, 1 equiv.) and 4-fluorobenzaldehyde 2 (3.6 g, 29 mmol, 1.87 equiv.) in a mixture of solvent THF (30 mL) and MeOH (5 mL) was added titanium(III) chloride (20% w/w solution in 2 N Hydrochloric acid) (80 mL, 6 equiv.) dropwise with stirring at room temperature. The reaction mixture was allowed to stir at 3050° C. for 2 h. Then the mixture was diluted with water (160 mL), the resulting solution was extracted with EtOAc (100 mL×4). The combined organic layers were washed with saturated $NaHCO_3$ (50 mL×3) and aqueous $NaHSO_3$ (100 mL×3), dried by $Na_2SO_4$, concentrated to afford a yellow solid, crude solid was washed by petrol ether (120 mL). After dried in vacuum, it afforded the title compound as a yellow solid (5.9 g, yield: 95%, Purity: 97%). LC-MS (ESI) m/z: 399 $(M+1)^+$. $^1$H-NMR (400 MHz, $CDCl_3$-d) δ (ppm): 3.58 (s, 3H), 3.87 (s, 3H), 4.16-4.19 (d, $J^2$=13.2 Hz, 1H), 4.88 (s, 1H), 5.37-5.40 (d, $J^2$=13.2 Hz, 1H), 6.47-6.53 (m, 2H), 6.97-7.01 (m, 2H), 7.37-7.41 (m, 2H), 7.80 (s, 1H).

Compound b was also prepared following a modified version of the above procedure where the washed combined organic layers were concentrated to 1-2 vols, and then 6 vols of heptane added, following which the wash, concentrating and adding heptane was repeated. The solution was then concentrated to 1-2 vols and 6 vols of MTBE added. This mixture was stirred for 1 hour and filtered to give a light yellow solid (92% yield, 98% purity).

Preparation of c. Chiral Separation of b to Obtain c was Achieved Using Supercritical Fluid Chromatography (SFC). Sample was prepared using methanol as a solvent (b: 45 mg/mL), by heated to 40-50° C. and filtrated before the injection. A CHIRALPAK IC, 250*30 mm (I.D.), column and $CO_2$/methanol (80/20) mobile phase was employed with a flow rate of 65 g/minute. The column temperature was maintained at 35° C. The desired fraction came out of the column as the first peak having a retention time of 2.3 minute and another enantiomer having a retention time of 4.3 minute. UV detection was at 254 nm. The recovery of c was about 92% with >98% ee.

(8S,9R)-5-Fluoro-8-(4-fluorophenyl)-9-(1-methyl-1H-1,2,4-triazol-5-yl)-8,9-dihydro-2H-pyrido[4,3,2-de]phthalazin-3(7H)-one. To a solution of c in methanol was added hydrazine monohydrate, and the mixture was stirred under 25° C. for 10 hr. Then the mixture was filtered and dried to obtain the title compound as a white solid. In certain instances where, rather than using methanol, acetonitrile (10 vols) with 3 equivalents of hydrazine monohydrate was used, the reaction could be finished in 5 hours at 35° C. Yields were about 77% to 80% following these procedures.

Preparation and Comparison of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one salt and Free Base Forms The following example provides the preparation and characterization of (8S,9R)-fluoro-8-(4-fluorophenyl)-9-(1-methyl-1H-1,2,4-triazol-5-yl)-8,9-dihydro-2H-pyrido[4,3,2-de]phthalazin-3(7H)-one salt and free base polymorphs. Properties of a tosylate salt are shown to be superior to those of other salt and free base forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one. These improved properties include, but are not limited to, presence of a single crystalline form, no solvation, high melting point, non-hygroscopicity, and/or thermal stability.

Salt forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one were prepared by treating the compound under a given condition with an acid. Salts forms, nos. 1-18, are identified in Table 1 below, where the acid used to treat (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one are provided in the column under "Acid," and the conditions used during treatment are provided in the column under "Condition."

Polymorphs of free base (8S,9R)-5-Fluoro-8-(4-fluorophenyl)-9-(1-methyl-1H-1,2,4-triazol-5-yl)-8,9-dihydro-2H-pyrido[4,3,2-de]phthalazin-3(7H)-one were prepared from solutions prepared with different solvents. Characterizations of free base forms, nos. 19-24, are summarized in Table 2 and paragraphs referring to Table 2.

Microscopy and other standard laboratory measurements were employed to characterize solid forms, melting temperatures, solvation and/or hydration, and other physiochemical properties (including, but not limited to, solubility, PKa, and Log P), of the salt forms and free base polymorphs.

TABLE 1

Salt forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one

| No. | Acid | Condition | Product | Yield, % |
|---|---|---|---|---|
| 1 | 2N HCl in $H_2O$. | MeOH, 2 h, precipitated from $CH_3CN$ | White powder | 64 |
| 2 | 3.3N HCl in THF | THF, dissolved at 60° C., HCl added at 5° C. | Pale yellow solid | 73 |
| 3 | Methanesulfonic acid ("MsOH") | MeOH—$CH_3CN$, 50° C.→25° C., 1 h | Yellow solid | 53 |
| 4 | p-touenesulfonic acid ("TsOH") | MeOH—$CH_3CN$, 50° C.→25° C., 2 h | Off white powder | 56 |
| 5 | TsOH | DCM-$CH_3CN$, 40° C.→25° C., 1 h | Off white powder | 95 |
| 6 | TsOH | Acetone, 60° C.→45° C.→25° C., 1 h | Off white powder | 62 |
| 7 | TsOH | THF, 60° C.→45° C.→25° C., 30 min | Off white powder | 69 |
| 8 | TsOH | acetone-THF, 60° C.→25° C., 0.5 h | white powder | 93 |
| 9 | Isethionic acid in isopropanol | MeOH-isoprapanol, 35° C., precipitated out through adding water | No salt formed | — |
| 10 | Isethionic acid in ethanol (0.62M) | MeOH, 35° C., precipitated out through adding water | No salt formed | — |
| 11 | Isethionic acid in ethanol (0.62M) | THF, 40° C., 10 min | White solid | 25 |
| 12 | Isethionic acid in ethanol (0.62M) | THF, 40° C., 10 min, standing overnight | White solid | 98 |
| 13 | Isethionic acid in ethanol (0.62M) | THF (dilute), 60° C., 10 min, precipitated quickly, standing overnight | White solid | 80 |
| 14 | Fumaric acid | MeOH, 30° C., 1.5 h | No salt formed | — |
| 15 | Fumaric acid | THF, 40° C., 40 min | No salt formed | — |
| 16 | 83% $H_3PO_4$ | MeOH, 32° C., 0.5 h, precipitated out through adding water | White powder | 40 |
| 17 | 83% $H_3PO_4$ | Acetone, 30-40° C., 1.5 h, precipitated out through adding water | White powder | 40 |
| 18 | 83% $H_3PO_4$ | Acetone-MeOH, 52° C., 20 min, standing at r.t. overnight, precipitated from Acetone-MeOH | | 64 |

TABLE 2

Solvents in preparing polymorphs of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one

| No. | Solvent | Form |
|---|---|---|
| 19 | Acetone | White powder |
| 20 | Methanol/ethyl acetate | White powder |
| 21 | Acetonitrile | White powder |
| 22 | Methanol | White powder |
| 23 | Isopropanol | Off white powder |
| 24 | DMSO/ethanol | Off white powder |

HCl Salt, 1: Microscopy: largely crystalline. Results based on microscopy, XRPD (Table 3), DSC (Table 4) and TGA (Table 5) suggest that this HCl salt is in mixed crystalline and amorphous forms and possibly solvated.

TABLE 3

X-Ray Powder Diffraction: Selected Peaks of 1*

| Angle, °2θ | d value, Å | Relative Intensity, % |
|---|---|---|
| 6.083 | 14.5174 | 76 |
| 12.259 | 7.21408 | 40.8 |
| 18.471 | 4.79966 | 22.1 |
| 21.609 | 4.10925 | 29.1 |
| 22.068 | 4.02473 | 24.6 |
| 22.392 | 3.96718 | 23.4 |
| 22.952 | 3.87167 | 100 |
| 25.765 | 3.45499 | 29.8 |
| 26.389 | 3.37471 | 27.9 |

*Peaks with Relative Intensity of less than 20% are not reported

TABLE 4

Results of Differential Scanning Calorimetry of 1
Ramp 10.00° C./min to 300.00° C.

| Onset, ° C. | Maximum, ° C. | Stop, ° C. | Area, J/g |
|---|---|---|---|
| 40.28 | 79.83 | 120 | 43.97 |
| 195.43 | 216.86 | 225.21 | 105.1 |
| 248.11 | 253.55 | 256.2 | 35.39 |

TABLE 5

Results of Thermogravimetric Analysis of 1
Ramp 10.00° C./min to 300.00° C.
Starting Temperature = 25.7° C.

| Temperature, ° C. | Weight Change, % |
|---|---|
| 120 | 1.45 |
| 164 | 4.068 |
| 225 | 9.125 |
| 238 | 9.214 |
| 252 | 9.265 |

Mesylate Salt, 3: Microscopy: mixed crystalline and amorphous. Melting point: 179~184° C. by melting point apparatus. Results based on microscopy, XRPD (Table 6), DSC (Table 7) and TGA (Table 8) suggest that this mesylate salt is in mixed forms and possibly solvated.

TABLE 6

X-Ray Powder Diffraction: Selected Peaks of 3*

| Angle, °2θ | d value, Å | Relative Intensity, % |
|---|---|---|
| 5.418 | 16.299 | 100 |
| 10.212 | 8.65532 | 20 |
| 16.526 | 5.35996 | 24 |
| 18.641 | 4.7561 | 40 |
| 19.176 | 4.62469 | 25.9 |
| 22.486 | 3.95078 | 26.9 |
| 27.956 | 3.18897 | 30.7 |

*Peaks with Relative Intensity of less than 20% are not reported

TABLE 7

Results of Differential Scanning Calorimetry of 3
Ramp 10.00° C./min to 300.00° C.

| Onset, ° C. | Maximum, ° C. | Stop, ° C. | Area, J/g |
|---|---|---|---|
| 25.9 | 66.91 | 152.71 | 167 |
| 173.02 | 178.7 | 186.83 | 32.12 |
| 193.88 | 205.29 | 234.02 | 47.6 |
| 240.14 | 250.24 | 255.91 | 34.84 |

TABLE 8

Results of Thermogravimetric Analysis of 3
Ramp 10.00° C./min to 300.00° C.
Starting Temperature = 25.64° C.

| Temperature, ° C. | Weight Change, % |
|---|---|
| 120 | 2.33 |
| 152 | 2.584 |
| 178 | 2.829 |
| 205 | 3.42 |
| 250 | 5.193 |

Tosylate Salt, 4, from methanol-acetonitrile: (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (190 mg, 0.5 mmol) was dissolved in MeOH (2 mL) and $CH_3CN$ (2 mL) at 50° C. TsOH (190 mg, 1 mmol), dissolved in a mixture of MeOH (2 mL) and $CH_3CN$ (2 mL), was then added. After 30 seconds, a white solid precipitated from the solution and the solution was allowed to cool to 25° C. Stirring was continued at 25° C. for approximately 2 h. The white solid was collected by filtration, washed with $CH_3CN$ (2 mL), and dried under vacuum at 45° C. for 3 days. Three preparations were made with yields of 47%, 56% and 56%, with similar results as determined by microscopy, XRPD, DSC and TGA (ramp 10.00° C./min to 300.00° C.). Results provided herein are from one of these preparations. Microscopy: crystalline. Results based on microscopy, XRPD (Table 9) and DSC (Table 10) suggest that this tosylate salt is substantially a single crystalline form.

TABLE 9

X-Ray Powder Diffraction: Selected Peaks of 4*

| Angle, °2θ | d value, Å | Relative Intensity, % |
|---|---|---|
| 7.420 | 11.90485 | 100.0 |
| 15.007 | 5.89882 | 12.1 |
| 17.702 | 5.00619 | 10.4 |

TABLE 9-continued

X-Ray Powder Diffraction: Selected Peaks of 4*

| Angle, °2θ | d value, Å | Relative Intensity, % |
|---|---|---|
| 18.011 | 4.92105 | 16.8 |
| 18.466 | 4.80095 | 8.2 |
| 18.980 | 4.67196 | 9.3 |
| 19.981 | 4.44018 | 37.8 |
| 20.328 | 4.36515 | 20.8 |
| 21.408 | 4.14726 | 10.6 |
| 22.580 | 3.93464 | 18.0 |
| 23.952 | 3.71229 | 23.2 |
| 24.755 | 3.59370 | 13.0 |

*Peaks with Relative Intensity of less than 8% are not reported

TABLE 10

Results of Differential Scanning Calorimetry of 4
Ramp 10.00° C./min to 400.00° C.

| Endotherm Onset, ° C. | Maximum, ° C. | Stop, ° C. | Area, J/g |
|---|---|---|---|
| 332.22 | 333.93 | 340.84 | 155.2 |

Tosylate Salt, 5, from dichloromethane-acetonitrile: (8S, 9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (120 mg, 0.316 mmol) was suspended in CH$_2$Cl$_2$ (5 mL) and CH$_3$CN (5 mL) at 40° C., then TsOH (66 mg, 0.348 mmol) was added, after adding, the solution was clear. After 5 seconds, a white solid was precipitated from the solution, continued to stir at 25° C. for 1 h, filtered to obtain the white crystal solid, the solid was washed by CH$_3$CN (2 mL), dried under vacuum at 45° C. for 3 days. Microscopy: birefringent, crystalline. Results based on microscopy, XRPD (Table 11), DSC (Table 12a and FIG. 3a), and TGA (Table 12b and FIG. 3b) suggest that this tosylate salt is substantially a single crystalline form.

TABLE 11

X-Ray Diffraction: Selected Peaks of 5*

| Angle, °2θ | d value, Å | Relative Intensity, % |
|---|---|---|
| 7.417 | 11.90865 | 100 |
| 15.021 | 5.89335 | 13.8 |
| 17.375 | 5.09992 | 10.3 |
| 17.739 | 4.99597 | 13.4 |
| 18.034 | 4.91502 | 23.1 |
| 18.54 | 4.78195 | 10.4 |
| 19.021 | 4.66202 | 11.8 |
| 20.075 | 4.41956 | 65.7 |
| 20.394 | 4.35116 | 28.4 |
| 21.436 | 4.14198 | 17.5 |
| 22.629 | 3.92624 | 20.6 |
| 23.999 | 3.70513 | 30.6 |
| 24.826 | 3.58348 | 15.4 |

*Peaks with Relative Intensity of less than 10% are not reported

TABLE 12a

Results of Differential Scanning Calorimetry of 5
Ramp 10.00° C./min to 400.00° C.

| Endotherm Onset, ° C. | Maximum, ° C. | Stop, ° C. | Area, J/g |
|---|---|---|---|
| 331.72 | 333.5 | 340.46 | 134.6 |

TABLE 12b

Results of TGA of 5
Ramp 10.00° C./min to 400.00° C.

| Start, ° C. | Start, % | Stop, ° C. | Stop, % | % Change in weight |
|---|---|---|---|---|
| 25.13 | 100.2 | 120 | 100.2 | 0.1231 |
| 25.13 | 100.2 | 250 | 100.2 | 0.2894 |
| 25.13 | 100.2 | 340.46 | 100.2 | 43.54 |

Tosylate Salt, 6, from acetone: (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (120 mg, 0.316 mmol) was suspended in acetone (15 mL) at 25° C. After heating to 60° C., the mixture became clear and the temperature was reduced to 45° C. TsOH (70 mg, 0.35 mmol) was then added, and after 30 seconds, a white solid was precipitated from the solution which was allowed to cool to 25° C. Stirring was continued at 25° C. for 1 h. The white crystal solid was collected by filtration, washed with acetone (8 mL), and dried under vacuum at 45° C. for 3 days. Microscopy: birefringent, crystalline. Results based on microscopy, XRPD (Table 13), DSC (Table 14a and FIG. 4a), and TGA (Table 14b and FIG. 4b) suggest that this tosylate salt is substantially a single crystalline form.

TABLE 13

X-Ray Powder Diffraction: Selected Peaks of 6*

| Angle, °2θ | d value, Å | Relative Intensity, % |
|---|---|---|
| 7.461 | 11.83921 | 100 |
| 12.474 | 7.09046 | 10.2 |
| 14.447 | 6.12594 | 23.7 |
| 15.092 | 5.86557 | 27.3 |
| 17.4 | 5.09252 | 19.6 |
| 17.741 | 4.99533 | 17.9 |
| 18.11 | 4.89433 | 29.4 |
| 18.529 | 4.78464 | 15.8 |
| 19.045 | 4.65619 | 22.1 |
| 20.092 | 4.41595 | 100 |
| 20.425 | 4.34457 | 38.1 |
| 21.464 | 4.13667 | 22.7 |
| 21.772 | 4.0787 | 22.4 |
| 22.626 | 3.92672 | 22.4 |
| 23.101 | 3.84709 | 12.9 |
| 24.03 | 3.70042 | 78.7 |
| 24.851 | 3.5799 | 17.2 |
| 26.96 | 3.30456 | 12 |
| 29.82 | 2.99375 | 13.6 |
| 31.304 | 2.85511 | 10.5 |

*Peaks with Relative Intensity of less than 10% are not reported

TABLE 14a

Results of Differential Scanning Calorimetry of 6
Ramp 10.00° C./min to 400.00° C.

| Endotherm Onset, ° C. | Maximum, ° C. | Stop, ° C. | Area, J/g |
|---|---|---|---|
| 327.04 | 329.59 | 338.56 | 141.6 |

TABLE 14b

Results of TGA of 6
Ramp 10.00° C./min to 400.00° C.

| Start, ° C. | Start, % | Stop, ° C. | Stop, % | % Change in weight |
|---|---|---|---|---|
| 25.2 | 100.1 | 120 | 100.1 | 0.0388 |
| 25.2 | 100.1 | 250 | 100.1 | 0.5425 |
| 25.2 | 100.1 | 338.56 | 100.1 | 24.56 |

Tosylate Salt, 7, from THF: (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (120 mg, 0.316 mmol) was suspended in THF (6 mL) at 25° C. After heating to reflux, the mixture became clear and the temperature was reduced to 45° C. TsOH (66 mg, 0.35 mmol) was then added, and after 1.5 min, a white solid was precipitated from the solution which was allowed to cool to 25° C. Stirring was continued at 25° C. for 30 min. The white crystal solid was collected by filtration, washed with $CH_2Cl_2$ (10 mL), and dried under vacuum at 45° C. for 3 days. Microscopy: birefringent, crystalline. Results based on microscopy, XRPD (Table 15), DSC (Table 16a and FIG. 5a), and TGA (Table 16b and FIG. 5b) suggest that this tosylate salt is substantially a single crystalline form.

TABLE 15

X-Ray Powder Diffraction: Selected Peaks of 7*

| Angle, °2θ | d value, Å | Relative Intensity, % |
|---|---|---|
| 7.49 | 11.79319 | 77.3 |
| 12.501 | 7.07487 | 10.2 |
| 14.435 | 6.13139 | 23 |
| 15.097 | 5.86364 | 22.7 |
| 17.375 | 5.09982 | 19.4 |
| 17.782 | 4.98388 | 15.7 |
| 18.095 | 4.89857 | 24.6 |
| 18.493 | 4.79388 | 13.6 |
| 19.079 | 4.64788 | 20.2 |
| 20.059 | 4.42307 | 100 |
| 20.397 | 4.35056 | 33.4 |
| 21.491 | 4.13147 | 21.8 |
| 21.763 | 4.08054 | 20.5 |
| 22.61 | 3.92944 | 20.3 |
| 23.054 | 3.85486 | 12.1 |
| 24.005 | 3.7041 | 71 |
| 24.839 | 3.5816 | 15.3 |
| 26.934 | 3.30766 | 10.7 |
| 29.822 | 2.99352 | 11.6 |

*Peaks with Relative Intensity of less than 10% are not reported

TABLE 16a

Results of Differential Scanning Calorimetry of 7
Ramp 10.00° C./min to 400.00° C.

| Endotherm Onset, ° C. | Maximum, ° C. | Stop, ° C. | Area, J/g |
|---|---|---|---|
| 319.51 | 321.73 | 334.02 | 131.2 |

TABLE 16b

Results of TGA of 7
Ramp 10.00° C./min to 400.00° C.

| Start, ° C. | Start, % | Stop, ° C. | Stop, % | % Change in weight |
|---|---|---|---|---|
| 25.5 | 100 | 120 | 100 | 0.2109 |
| 25.5 | 100 | 250 | 100 | 2.552 |
| 25.5 | 100 | 334 | 100 | 26.55 |

Tosylate Salt, 8, from acetone-THF: (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (400 mg, 1.05 mmol) was suspended in a mixture of acetone (27 mL) and THF (13 mL) at 25° C., after heating to reflux, the reaction mixture became clear. Then TsOH (220 mg, 1.16 mmol) was added, after 30 seconds, a white solid was precipitated from the solution, continued stirring at 25° C. for 30 min, filtered to obtain the white crystal solid, which was washed by a mixture of acetone (10 mL) and 1,4-dioxane (4 mL), dried under vacuum at 45° C. for 3 days. Microscopy: birefringent, crystalline. Results based on microscopy, XRPD (Table 17 and FIG. 8), DSC (Table 18a and FIG. 2a), and TGA (Table 18b and FIG. 2b) suggest that this tosylate salt is substantially a single crystalline form. DVA was performed on this polymorph and showed a 0.1574% weight gain from 0%-95% RH (FIG. 8).

TABLE 17

X-Ray Powder Diffraction: Selected Peaks of 8*

| Angle, °2θ | d value, Å | Relative Intensity, % |
|---|---|---|
| | | 100 |
| 12.509 | 7.07056 | 2.7 |
| 14.478 | 6.11288 | 2.5 |
| 15.119 | 5.85526 | 6.9 |
| 17.381 | 5.09812 | 3 |
| 17.782 | 4.98407 | 7.3 |
| 18.172 | 4.87778 | 11.5 |
| 18.584 | 4.77078 | 4.2 |
| 19.114 | 4.63967 | 4.6 |
| 20.087 | 4.41697 | 15.5 |
| 20.538 | 4.32097 | 12.3 |
| 21.538 | 4.12263 | 4.8 |
| 21.862 | 4.06217 | 2.7 |
| 22.649 | 3.92287 | 16.3 |
| 23.194 | 3.83181 | 2.4 |
| 24.077 | 3.69326 | 8.7 |
| 24.864 | 3.57812 | 7.6 |
| 26.984 | 3.30157 | 5 |
| 29.974 | 2.97873 | 3.4 |
| 30.443 | 2.93386 | 2.2 |
| 30.844 | 2.89668 | 2.3 |
| 32.065 | 2.7891 | 3.5 |
| 32.49 | 2.75357 | 2.2 |
| 37.563 | 2.39253 | 2.2 |

*Peaks with Relative Intensity of less than 2% are not reported

TABLE 18a

Results of Differential Scanning Calorimetry of 8
Ramp 10.00° C./min to 400.00° C.

| Endotherm Onset, ° C. | Maximum, ° C. | Stop, ° C. | Area, J/g |
|---|---|---|---|
| 330.73 | 333.43 | 334.1 | 252.6 |

TABLE 18b

Results of TGA of 8
Ramp 10.00° C./min to 400.00° C.

| Start, ° C. | Start, % | Stop, ° C. | Stop, % | % Change in weight |
|---|---|---|---|---|
| 24.9 | 99.81 | 120 | 99.81 | 0.06696 |
| 24.9 | 99.81 | 274.33 | 99.81 | 2.071 |
| 24.9 | 99.81 | 320 | 99.81 | 19.97 |
| 24.9 | 99.81 | 335 | 99.81 | 34.56 |
| 24.9 | 99.81 | 363.03 | 99.81 | 50.39 |
| 24.9 | 99.81 | 394.92 | 99.81 | 54.39 |

Figure 1:
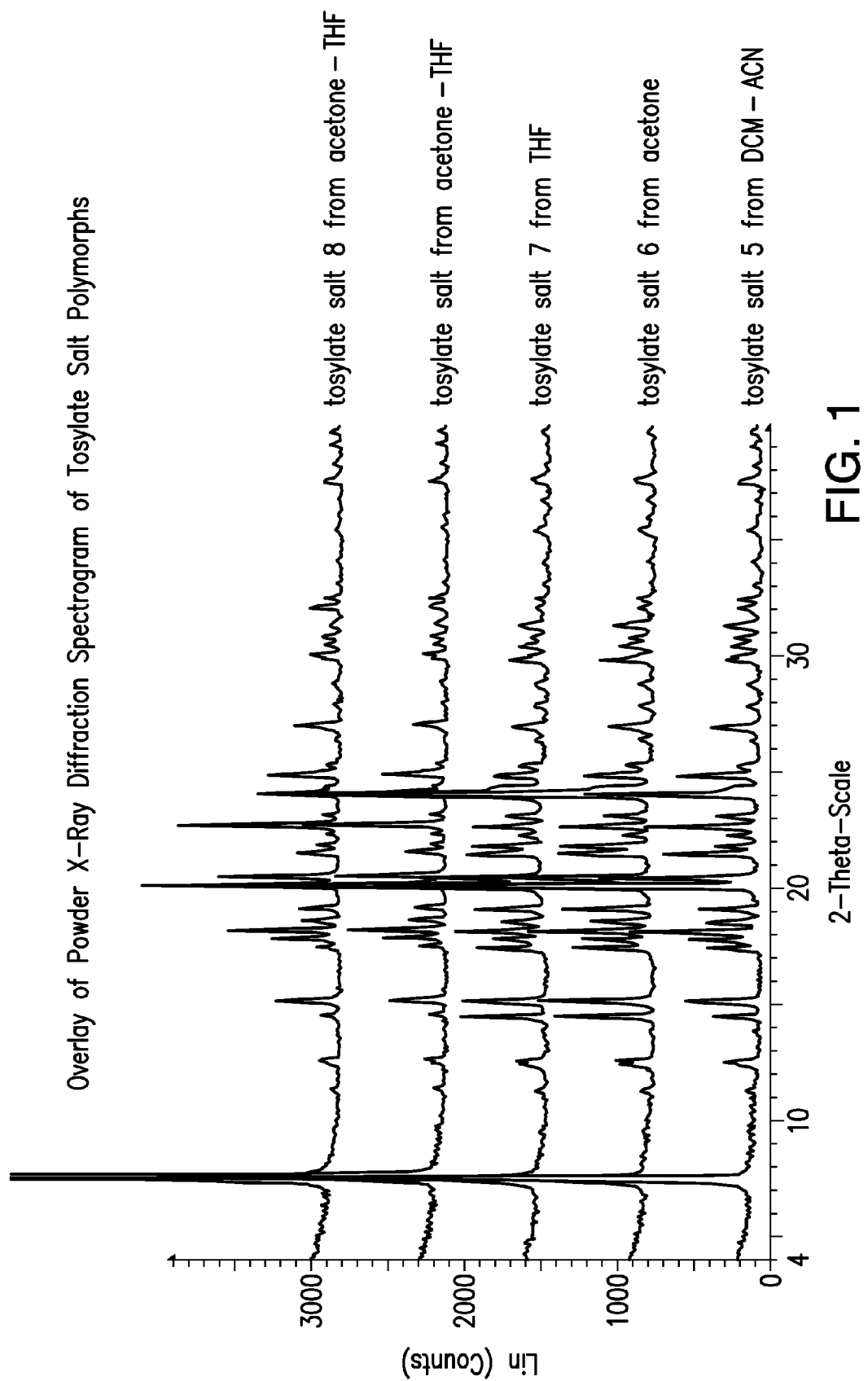
FIG. 1 provides an overlay of five examples of powder X-ray powder diffraction (XRPD) patterns of crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt.
Figure 2A:
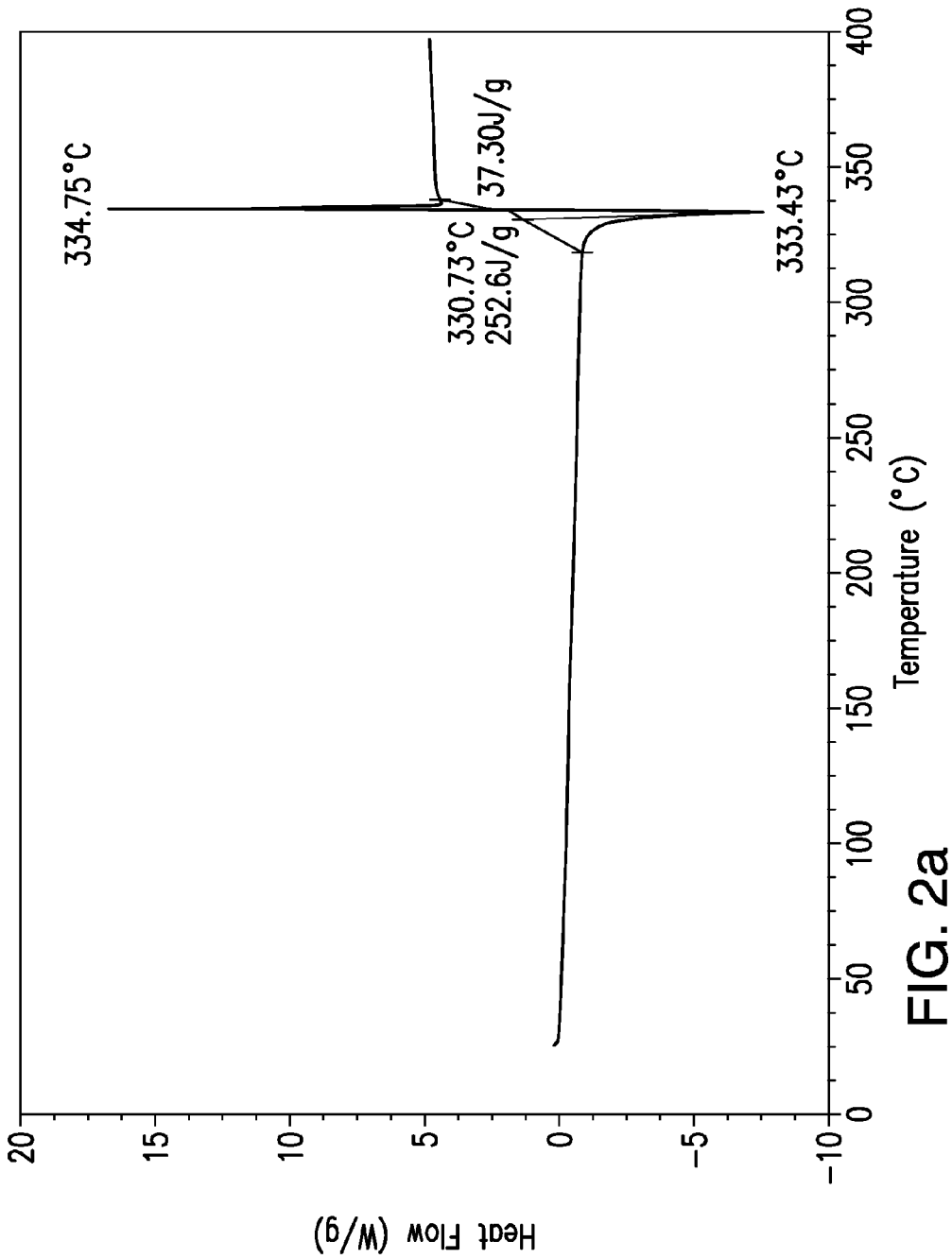
FIG. 2a provides a differential scanning calorimetric (DSC) graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 8, from acetone-THF preparation.
Figure 2B:
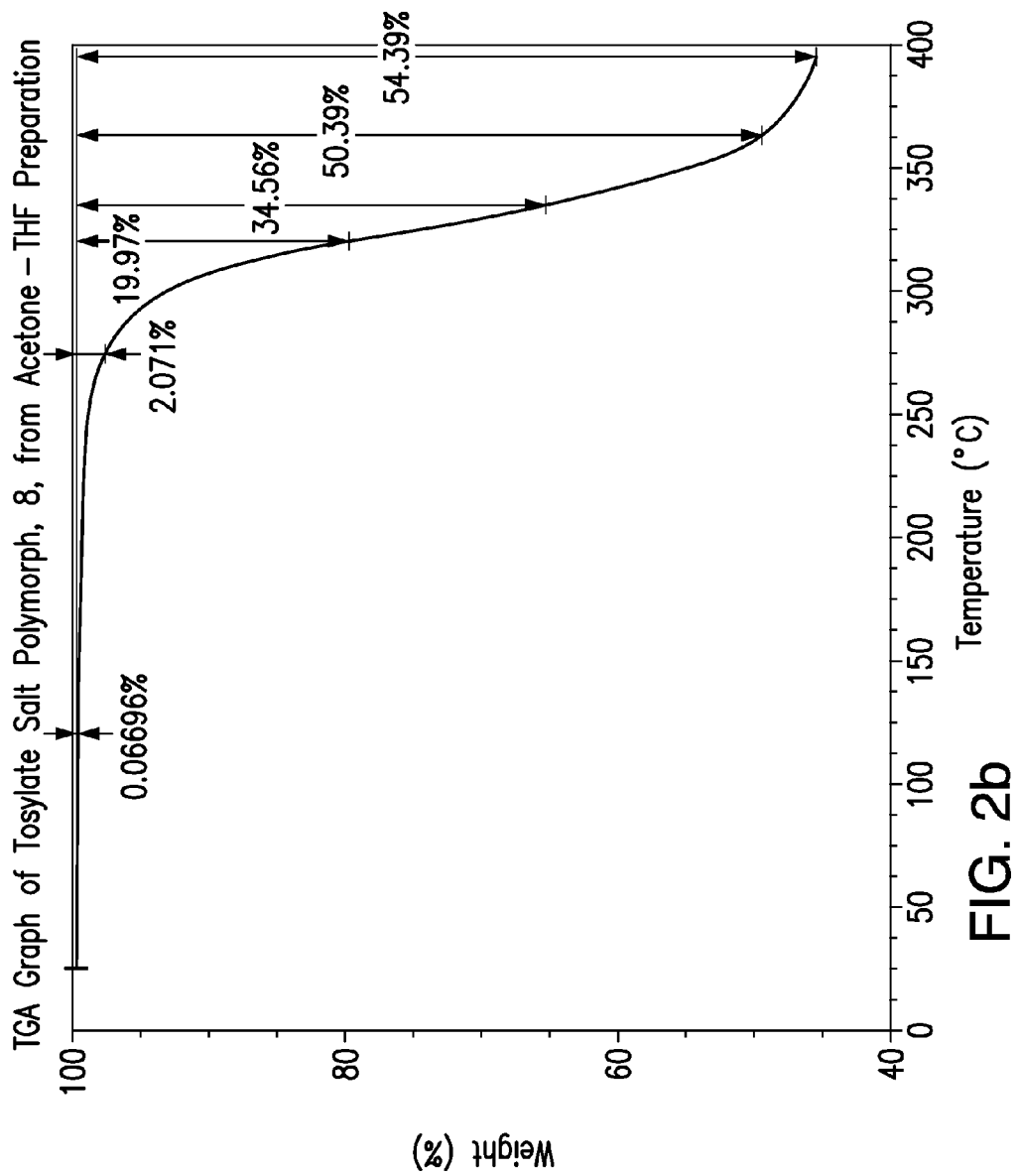
FIG. 2b provides a thermogravimetric analysis (TGA) graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 8, from acetone-THF preparation.
Figure 3B:
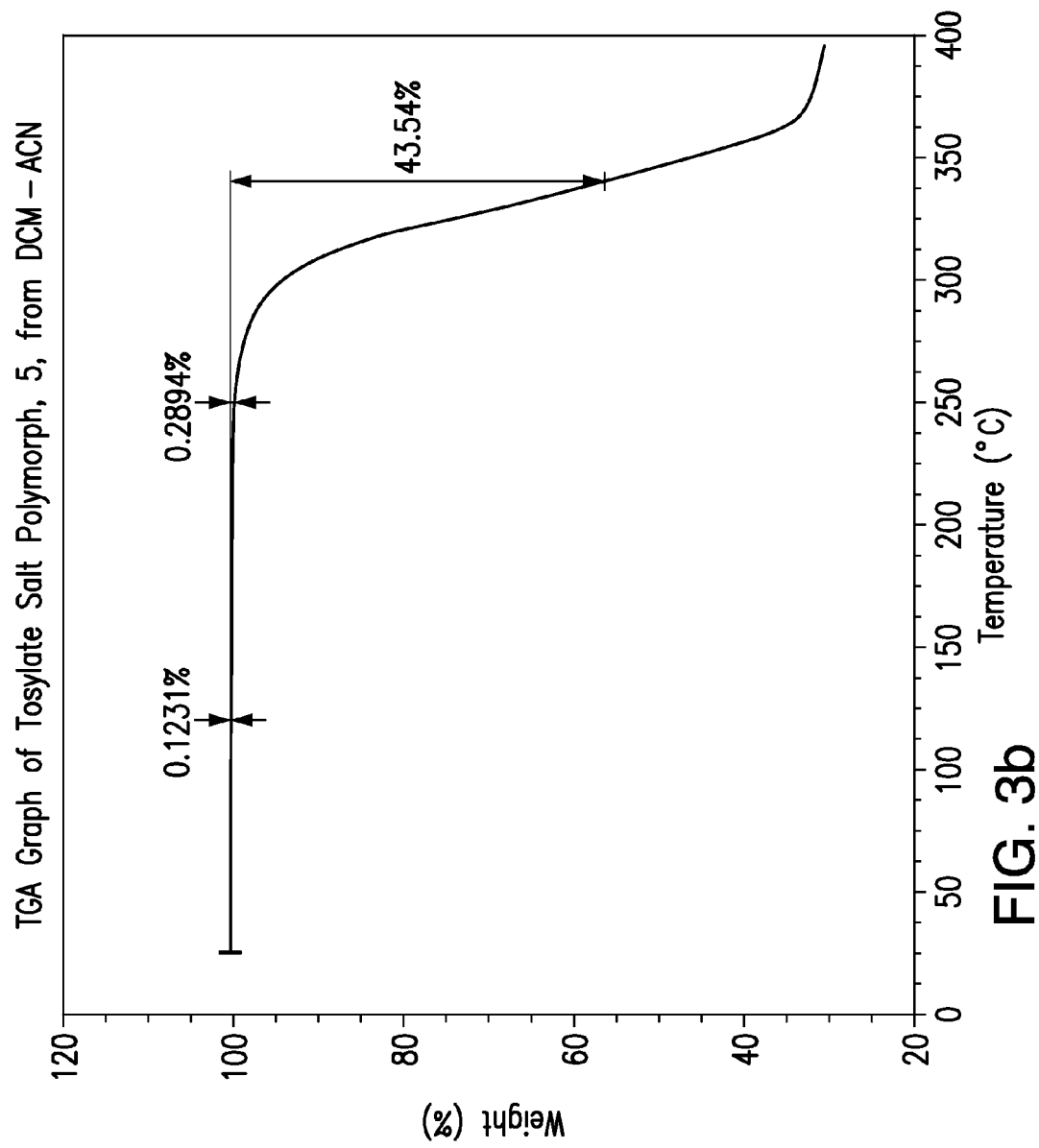
FIG. 3b provides a TGA graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 5, from DCM-ACN preparation.
Figure 4B:
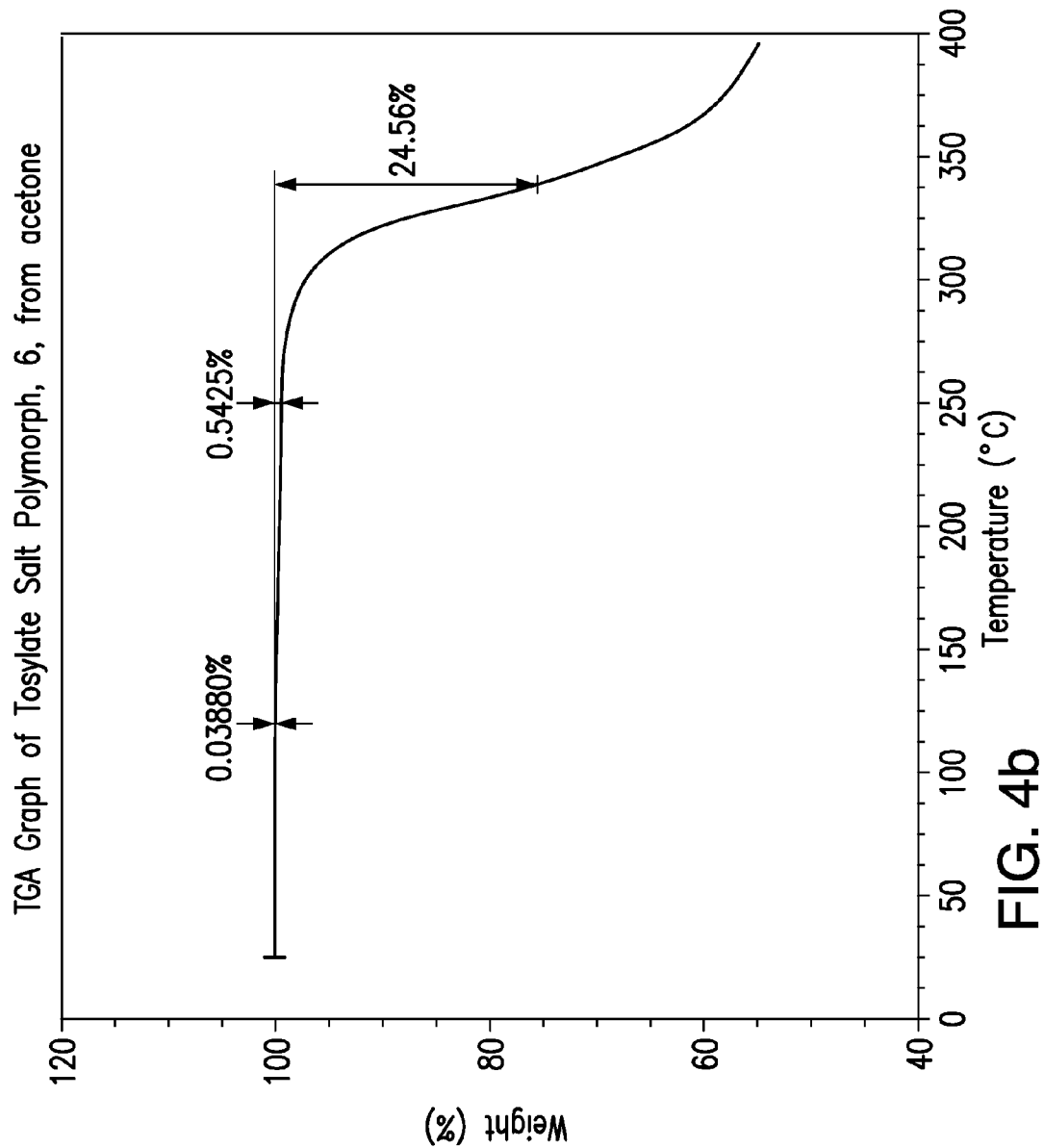
FIG. 4b provides a TGA graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt polymorph, 6, from acetone preparation.
Figure 5A:
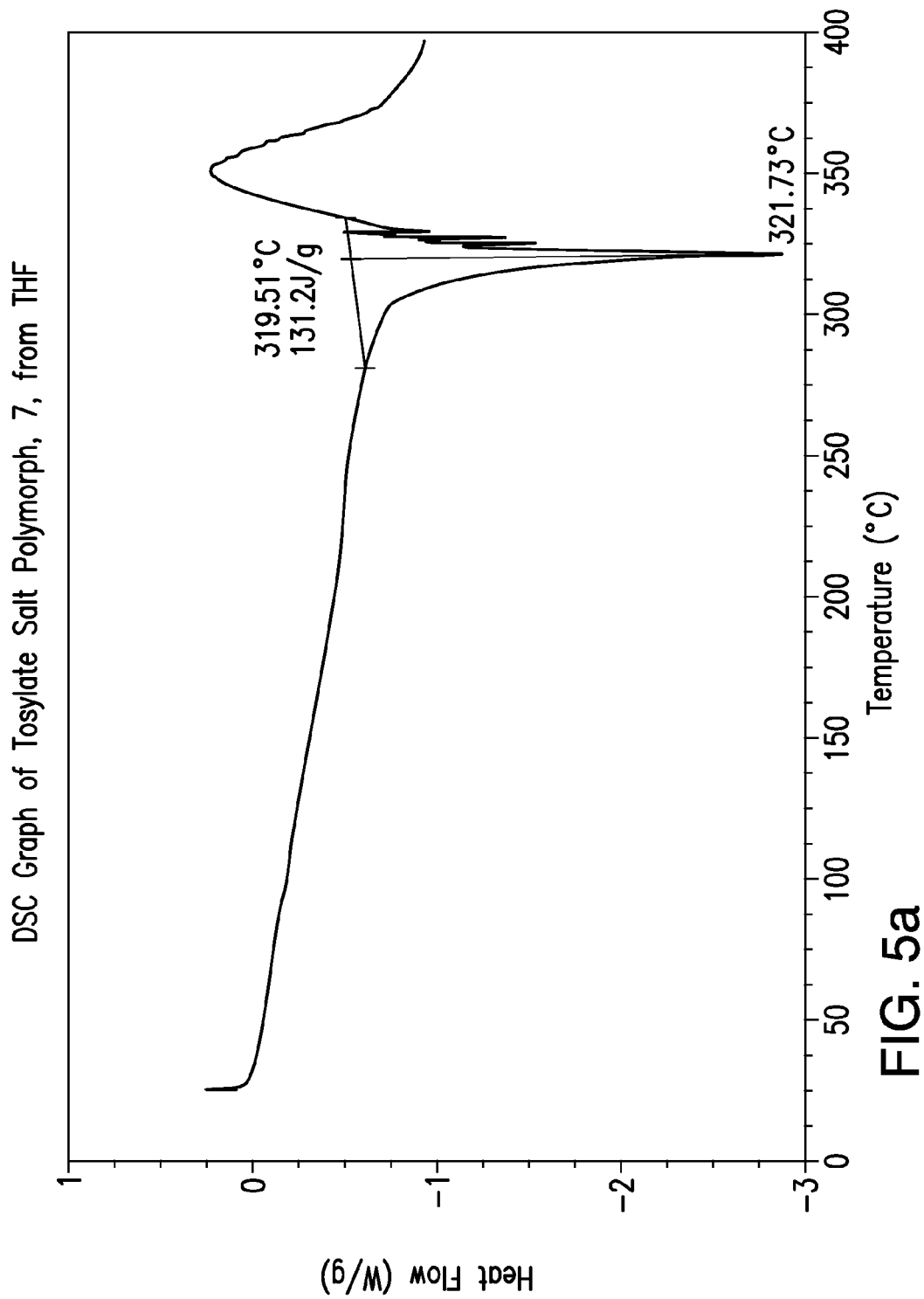
FIG. 5a provides a DSC graph of a crystalline (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7M-one tosylate salt polymorph, 7, from THF preparation.
Figure 5B:
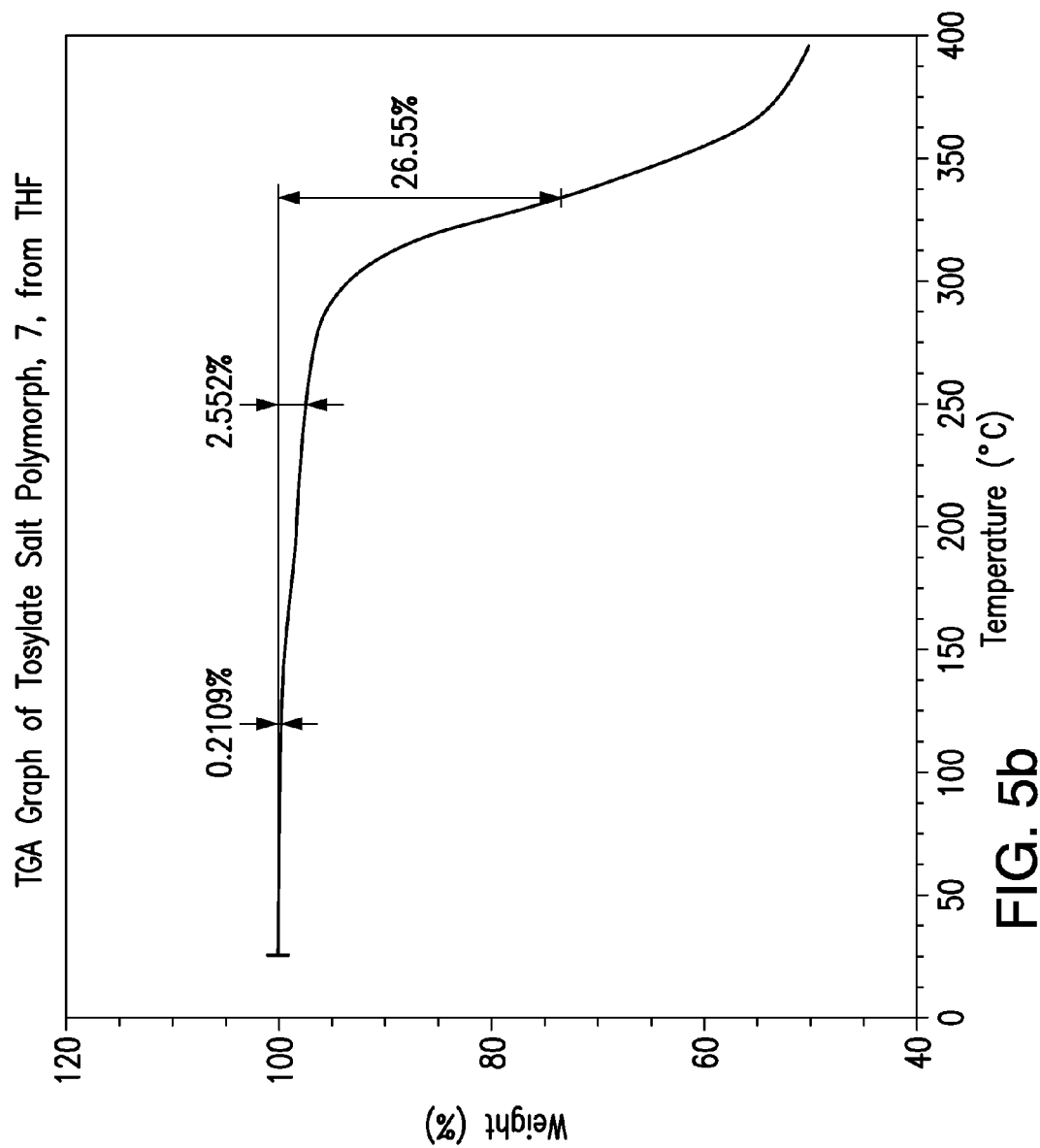
FIG. 5b provides a TGA graph of a crystalline (8S,9R)-5-fluoro-8-(4-fluorophenyl)-9-(1-methyl-1H-1,2,4-triazol-5- yl)-8,9-dihydro-2H-pyrido[4,3,2-de]phthalazin-3(7H)-one tosylate salt polymorph, 7, from THF preparation.

The XRPD peaks from preparations of crystalline tosylate salt forms 4, 5, 6, 7, and 8 are similar. Overlay of XRPD graphs for 5, 6, 7, and 8 are shown in FIG. 1. Each tosylate salt form 4, 5, 6, 7, and 8 had a single endothermic peak above 300° C. as determined by DSC, whereas other salt and free base forms all had endothermic peaks well below 300° C. These results indicate a single relatively stable polymorph exists for the tosylate salt of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one.

Isethionic Salt, 11, 12 and 13, from THF: Microscopy: crystalline. DSC results were not consistent between 11, 12 and 13, although all three preparation had at least 2, sometimes 3, endothermic peaks, including a broad endothermic peak below 150° C. and a sharp endothermic in the vicinity of 272° C. to 282° C. Unlike the tosylate salts described above, which did not show any weight change below 200° C. by TGA, isethionic salt 11 had a 5.72% weight loss at 134.8° C., and isethionic salt 12 showed a 7.034% weight loss at 139.06° C. Results obtained on the isethionic salts suggest that this salt form exists in more than one form.

Phosphate Salt, 16, 17 and 18: Microscopy, XRPD and DSC results were consistent with mixed crystalline and amorphous forms being present in each of the three phosphate salt preparations.

Free base, 19, from acetone: Microscopy, XRPD and DSC results were consistent with a mixture of forms.

TABLE 19

X-Ray Powder Diffraction: Selected Peaks of free base 19*

| Angle, °2θ | d value, Å | Relative Intensity, % |
|---|---|---|
| 5.128 | 17.21795 | 62.4 |
| 8.987 | 9.83224 | 100 |
| 10.383 | 8.5132 | 39.2 |
| 20.388 | 4.3525 | 30 |
| 22.851 | 3.88849 | 48.2 |

*Peaks with Relative Intensity of less than 30% are not reported

TABLE 20

Results of Differential Scanning Calorimetry of free base 19
Ramp 10.00° C./min to 300.00° C.

| Onset, ° C. | Maximum, ° C. | Stop, ° C. | Area, J/g |
|---|---|---|---|
| 26.5 | 67.29 | 120 | 71.07 |
| 164.92 | 171.21 | 174.32 | 4.897 |
| 176.16 | 180.39* | 185.4 | 20.58 |
| 251.82 | 255.36 | 258.76 | 50.61 |

*Exothermic

TABLE 21

Results of Thermogravimetric Analysis of free base 19
Ramp 10.00° C./min to 300.00° C.
Starting Temperature = 25.64° C.

| Temperature, ° C. | Weight Change, % |
|---|---|
| 120 | 1.054 |
| 161 | 4.256 |
| 174 | 5.977 |
| 185 | 7.82 |
| 238 | 8.874 |

Free base, 20, from MeOH/EtOAc: Microscopy showed birefringent crystalline form; XRPD and DSC results were consistent with a mixture of forms.

TABLE 22

X-Ray Powder Diffraction: Selected Peaks of free base 20*

| Angle, °2θ | d value, Å | Relative Intensity, % |
|---|---|---|
| 5.181 | 17.04465 | 83.7 |
| 9.021 | 9.79532 | 100 |
| 10.427 | 8.47684 | 23.3 |
| 18.855 | 4.70265 | 43.9 |
| 22.836 | 3.89114 | 43.3 |

*Peaks with Relative Intensity of less than 14% are not reported

TABLE 23

Results of Differential Scanning Calorimetry of free base 20
Ramp 10.00° C./min to 300.00° C.

| Onset, ° C. | Maximum, ° C. | Stop, ° C. | Area, J/g |
|---|---|---|---|
| 37.21 | 76.28 | 111.48 | 104.2 |
| 163.49 | 170.11 | 174.03 | 2.886 |
| 177.94 | 181.36* | 189.67 | 23.47 |
| 249.57 | 253.69 | 256.48 | 52.94 |

*Exothermic

TABLE 24

Results of Thermogravimetric Analysis of free base 20
Ramp 10.00° C./min to 300.00° C.
Starting Temperature = 25.64° C.

| Temperature, ° C. | Weight Change, % |
|---|---|
| 120 | 1.926 |
| 174.03 | 3.167 |
| 189.67 | 3.234 |
| 256.48 | 3.448 |

Free base form 21, from acetonitrile: A mixture of crystalline and amorphous forms was observed. DSC: broad endotherm with maximum near 133.05° C., exotherm maximum near 209.21° C. and sharp endotherm with maximum at 253.85° C. TGA: weight loss, at 142.46° C. was 3.7%, and at 256.48° C. was 4.259%. The d values in angstroms (Å) for peaks, greater than 19% relative intensity, resolved by XRPD were as follows: 16.58486; 11.49904; 6.33021; and 6.01178.

Free base form 22, from methanol: A mixture of crystalline and amorphous forms with properties similar to that of free base form 20 was observed.

Free base form 23, from isopropanol: The material produced was amorphous.

Free base form 24, from DMS/ethanol: A mixture of crystalline and amorphous forms was observed. DSC: endotherm peaks: 52.20° $C_{.max}$ (12.54 J/g); 202.63° $C_{.max}$ (120.9 J/g); 249.34° $C_{.max}$ (40.65 J/g). TGA: ambient to 120° C., 0.9388% weight loss; at 223.8° C., 17.47% weight loss.

These results demonstrate that crystalline forms of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3 (7H)-one free base can be prepared from certain solvents, however these preparations were found not to be single crystalline forms having stability matching that of a crystalline tosylate salt form provided herein.

Exemplary Preparation of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt The following exemplifies a process suitable for GMP large scale production of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one mono-tosylate salt as a single crystalline form.

Variation 1: To a solution of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (12.4 g) in THF (40 vols) was slowly added a solution of TsOH (1.05 equiv.) in THF (5 vols) at 50° C.~54° C. The mixture was stirred for additional 30 minutes at this temperature. The mixture was then concentrated down to 3~5 vols by distillation at 30° C.-40° C. under reduced pressure (vacuum:—0.07 MPa~−0.08 MPa). Further removal of THF solvent was achieved by adding acetone (20 vols) and then distilling down to 3~5 vols under reduced pressure, which was repeated three times. The mixture was cooled down to 5° C. and filtered under nitrogen protection. The solid was dried at 60° C. for 17 hours. It gave the title compound as a white crystal solid (16.0 g, 89% yield). LC-MS (ESI) m/z: 381 (M+1)$^+$. $^1$H-NMR (400 MHz, DMSO-$d_6$) δ (ppm): 2.29 (s, 3H), 3.67 (s, 3H), 4.97-5.06 (m, 2H), 6.91-6.94 (dd, $J^1$=2, $J^2$=10.8 Hz, 1H), 7.06-7.19 (m, 5H), 7.19-7.51 (m, 4H), 7.74 (s, 1H), 7.87 (s, 1H), 10.32 (brs, 1H), 12.36 (s, 1H).

Variation 2: To a solution of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (0.24 kg) in THF (40 vols) was slowly added a solution of TsOH (1.05 equiv.) in THF (5 vols) at 50° C.~54° C. The mixture was stirred for additional 30 minutes at this temperature. The mixture was then concentrated down to 3~5 vols by distillation at 30° C.-40° C. under reduced pressure (vacuum:—0.07 MPa~−0.08 MPa). Further removal of THF solvent was achieved by adding acetone (20 vols) and then distilling down to 3~5 vols under reduced pressure, which was repeated three times. After removal of THF solvent and distilling, the mixture was re-slurried with 12 vols of acetone for 14~15 hours at 50° C.~54° C. The mixture was then cooled down to 5° C. and filtered under nitrogen protection. The solid was dried at 60° C. for 17 hours. It gave the title compound as a white crystal solid (0.31 kg, 91.7% yield, 99.65% purity).

When subject to $^1$H-NMR, the one-to-one integration ratio of N-methyl at 3.67 ppm from the free-base and the methyl at 2.29 ppm from toluene sulfonic acid suggests a mono-tosylate salt formation.

When subjected to DVS at 25° C., the tosylate salt produced from using the steps described in Variation 2 showed negligible weight gain (less than 1%) of the tosylate salt as humidity was increased from 0% to 95% which suggests that it is not hygroscopic. (See Table 29.)

The XRPD pattern in FIG. 6 was collected with a PANalytical X'Pert PRO MPD PW3040 diffractometer using an incident beam of Cu radiation produced using an Optix long, fine-focus source. An elliptically graded multilayer mirror was used to focus Cu Kα X-rays (1.54059 Å) through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge were used to minimize the background generated by air. Soller slits (0.02×0.02 radians) for the incident and diffracted beams were used to minimize broadening from axial divergence. Diffraction patterns were collected using a scanning position-sensitive detector (X'Celerator) located 240 mm from the specimen and Data Collector software v. 2.2b. The XRPD data acquisition parameters are: transmission mode, X-ray tube settings of 45 kV and 40 mA, 1.00-39.99°2θ scan range, 0.017°2θ step size, 1939 seconds collection time, 1.2°/minute scan speed, ½° divergence slit, and 1.0 second sample revolution time. The entire list of peaks identified in the XRPD pattern, or a subset thereof, may be sufficient to characterize the polymorph(s) obtained. Results provided for XRPD (Table 25) are for a tosylate salt prepared using the steps described in Variation 2. The data in Table 25 are from the XRPD spectrogram provided in FIG. 6.

DSC analyses were performed on the tosylate salts prepared using variation 1 and variation 2 above and similar results were observed.

A DSC thermogram for tosylate salt prepared using the steps described in Variation 2 was acquired using a Mettler Toledo Differential Scanning calorimeter 1. The temperature was ramped from 25° C. to 400° C. at 10° C./minute. In the DSC figure, exothermic events are plotted in the upward direction. The data in Table 26 are from the DSC graph provided in FIG. 7a. The thermogram shows a very sharp onset of melting, and an exotherm after the completion of melting indicates that melting occurs with decomposition. The flat baseline prior to reaching the melting onset indicates no thermal transitions before melting, suggesting no solvate formation and no transformation of one crystalline form to another.

A TGA thermogram for tosylate salt prepared using the steps described in Variation 2 was acquired using a Mettler Toledo Thermogravimetric Analyzer/Differential Scanning calorimeter 1. The temperature was ramped from 25° C. to 400° C. at 10° C./minute. The TGA graph is provided in FIG. 7b. The trace shows a stable baseline up to the start of melting and decomposition. This indicates that there is little if any residual solvent or absorbed water present in the crystalline product, and that the product is stable to heat, prior to the onset of decomposition at the melting point.

The solid-state $^{13}$C cross polarization magic angle spinning (CP/MAS) NMR spectrum for the tosylate salt prepared using the steps described in Variation 2 was acquired at 25° C. on a Varian $^{UNITY}$INOVA-400 spectrometer (Larmor frequencies: $^{13}$C=100.543 MHz, $^{1}$H=399.787 MHz). The sample was packed into a 4 mm PENCIL type zirconia rotor and rotated at 12 kHz at the magic angle. The spectrum was acquired with phase modulated SPINAL-64 high power $^{1}$H decoupling during the acquisition time using a $^{1}$H pulse width of 2.6 µs (90°), a ramped amplitude cross polarization contact time of 5 ms, a 30 ms acquisition time, a 20 second delay between scans, a spectral width of ~45 kHz with 2799 data points, and with 400 co-added scans. The free induction decay (FID) was processed using Varian/Agilent VNMR 6.1C software with 65536 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm. The entire list of peaks identified in the $^{13}$C NMR spectrum, or a subset thereof, may be sufficient to characterize the polymorph(s) obtained. The data in Table 28 are from the spectrum provided in FIG. 12.

TABLE 25

XRPD: Selected Peaks of Tosylate Salt prepared from Large Scale Process*

| Angle, °2θ (±0.2 2θ) | d value, Å | Relative Intensity, % |
|---|---|---|
| 7.22 | 12.242 ± 0.348 | 6 |
| 7.51 | 11.780 ± 0.322 | 46 |
| 9.49 | 9.316 ± 0.200 | 2 |
| 11.27 | 7.855 ± 0.142 | 2 |
| 12.35 | 7.166 ± 0.117 | 8 |
| 12.52 | 7.071 ± 0.114 | 7 |
| 13.82 | 6.407 ± 0.094 | 1 |
| 14.47 | 6.120 ± 0.085 | 18 |
| 15.14 | 5.851 ± 0.078 | 15 |
| 17.41 | 5.092 ± 0.059 | 9 |
| 17.62 | 5.035 ± 0.057 | 3 |
| 17.78 | 4.988 ± 0.056 | 5 |
| 18.12 | 4.897 ± 0.054 | 10 |
| 18.53 | 4.787 ± 0.052 | 6 |
| 19.07 | 4.654 ± 0.049 | 9 |
| 20.09 | 4.420 ± 0.044 | 100 |
| 20.46 | 4.342 ± 0.042 | 13 |
| 21.48 | 4.138 ± 0.038 | 17 |
| 21.81 | 4.075 ± 0.037 | 12 |
| 22.26 | 3.994 ± 0.036 | 6 |
| 22.65 | 3.927 ± 0.035 | 5 |
| 23.10 | 3.851 ± 0.033 | 8 |
| 24.05 | 3.701 ± 0.031 | 53 |
| 24.25 | 3.670 ± 0.030 | 6 |
| 24.83 | 3.585 ± 0.029 | 6 |
| 25.25 | 3.527 ± 0.028 | 5 |
| 26.37 | 3.380 ± 0.025 | 2 |
| 26.77 | 3.330 ± 0.025 | 2 |
| 26.96 | 3.308 ± 0.024 | 3 |
| 27.84 | 3.204 ± 0.023 | 3 |
| 28.64 | 3.116 ± 0.021 | 1 |
| 28.78 | 3.102 ± 0.021 | 2 |
| 29.18 | 3.061 ± 0.021 | 1 |
| 29.81 | 2.997 ± 0.020 | 8 |

*Peaks with Relative Intensity of less than 2% are not reported

TABLE 26

Results of DSC of Tosylate Salt prepared from Large Scale Proces
Ramp 10.00° C./min from 25.00 to 400.00° C.

| Endotherm Onset, °C. | Maximum, °C. | Stop, °C. | Area, J/g |
|---|---|---|---|
| 331.41 | 334.54 | 337.78 | −184.73 |

TABLE 28

Results of Solid State $^{13}$C NMR of Tosylate Salt prepared from Large Scale Process

| PPM | Height |
|---|---|
| 166.911 | 32.9 |
| 164.316 | 60.5 |
| 162.171 | 30.3 |
| 160.573 | 76.8 |
| 151.804 | 81.5 |
| 149.359 | 71.3 |
| 143.198 | 54.1 |
| 140.166 | 143.0 |
| 139.142 | 122.0 |
| 135.959 | 110.3 |
| 131.752 | 85.5 |
| 129.361 | 83.6 |
| 128.597 | 93.3 |
| 127.736 | 140.3 |
| 123.857 | 128.3 |
| 116.822 | 56.8 |
| 115.142 | 62.6 |
| 112.219 | 80.5 |
| 105.212 | 68.7 |
| 100.335 | 61.4 |
| 58.483 | 68.6 |
| 45.288 | 90.8 |
| 37.379 | 102.1 |
| 23.911 | 123.0 |

TABLE 29

Results of DVS Isotherm of Tosylate Salt prepared from Large Scale Process

| Target % | Change in Mass (%) | | |
|---|---|---|---|
| P/Po | Sorption | Desorption | Hysteresis |
| 0.0 | 0.0002 | −0.0015 | |
| 5.0 | 0.0214 | 0.0203 | −0.0011 |
| 10.0 | 0.0301 | 0.0326 | 0.0025 |
| 15.0 | 0.0375 | 0.0421 | 0.0045 |
| 20.0 | 0.0529 | 0.0513 | −0.0016 |
| 25.0 | 0.0617 | 0.0649 | 0.0033 |
| 30.0 | 0.0698 | 0.0791 | 0.0092 |
| 35.0 | 0.0812 | 0.0947 | 0.0134 |
| 40.0 | 0.1043 | 0.1084 | 0.0042 |
| 45.0 | 0.1233 | 0.1266 | 0.0033 |
| 50.0 | 0.1451 | 0.1456 | 0.0005 |
| 55.0 | 0.1641 | 0.1668 | 0.0027 |
| 60.0 | 0.1842 | 0.1895 | 0.0053 |
| 65.0 | 0.2127 | 0.2192 | 0.0065 |
| 70.0 | 0.2450 | 0.2535 | 0.0085 |
| 75.0 | 0.2798 | 0.2919 | 0.0121 |
| 80.0 | 0.3253 | 0.3402 | 0.0149 |
| 85.0 | 0.3922 | 0.4113 | 0.0190 |
| 90.0 | 0.4983 | 0.5230 | 0.0247 |
| 95.0 | 0.7473 | 0.7473 | |

BIOLOGICAL EXAMPLES

Example 1

Single-Agent Cytotoxicity Assay in Mantle Cell Lymphoma Cell Line

Mantle cell lymphoma cell line Granta-519 was cultured in Dulbecco's MEM (4.5 g/L glucose) containing 10% FBS, 2 mM L-glutamine, 100 U/mL Penicillin and 100 μg/mL Streptomycin. Mantle cell lymphoma cell line Jeko-1 was cultured in RPMI1640 containing 10% FBS, 100 U/mL Penicillin and 100 μg/mL Streptomycin. Mantle cell lymphoma cell line Z138 was cultured in IMDM containing 10% horse serum, 100 U/mL Penicillin and 100 μg/mL Streptomycin. All cell lines were maintained in 37° C. incubator with 5% $CO_2$ till ready for assay. Granta-519, Jeko-1 and Z138 cells were seeded at either 1000 or 5000 cells/well in 96-well plates. Cells were incubated for overnight at 37° C. before treated with their corresponding growth media containing free base in 0.1% DMSO at various concentrations ranging from 1000 nM to 0.32 nM. 0.1% DMSO was used as mock treatment or control. After 4 days incubation, cell survival was measured by CellTiter Glo (Promega) and cell survival fraction was calculated relative to control. GraphPad Prism5 software was used to plot data and calculate $IC_{50}$ values. See FIGS. 10a and 10b.

TABLE 28

| | $IC_{50}$ (nM) for 4-day assays | | |
|---|---|---|---|
| Cell Density | Jeko-1 | Granta-519 | Z-138 |
| 5000/well | 356.96 | 8.83 | 59.40 |
| 1000/well | 64.20 | 1.70 | 10.43 |

Example 2

Single-Agent Cytotoxicity Assay in Head & Neck Tumor Cell Lines

Oral squamaous carcinoma HSC-3 and HSC-4 cells were cultured in MEM+10% FBS. Oral squamaous carcinoma CAL 27 was cultured in DMEM+10% FBS. Basaloid squamous cell line PE/CA-PJ34 (clone 12) was cultured in IMDM+10% FBS. All cell lines were maintained in their corresponding growth media containing 100 U/mL Penicillin and 100 μg/mL Streptomycin in 37° C. incubator with 5% $CO_2$ till ready for assay. According to individual cell line growth rate, cells were seeded at different densities as indicated in each graph in 96-well plates in the time of assay. Cells were incubated for overnight at 37° C. before treated with their corresponding growth media containing free base in 0.1% DMSO at various concentrations ranging from 5000 nM to 0.064 nM. 0.1% DMSO was used as mock treatment or control. Media and compound were replenished every 5 days. After incubation for 7, 10, 11 or 13 days (as indicated in each graph), cell survival was measured by CellTiter Glo (Promega) and cell survival fraction was calculated relative to control. GraphPad Prism5 software was used to plot data and calculate $IC_{50}$ values. See FIGS. 11a and 11b.

TABLE 29

| | $IC_{50}$ (nM) | | |
|---|---|---|---|
| Cell Line | Days | Cell Density | $IC_{50}$ |
| HSC-4 | 7 | 100/well | 58 |
| | 11 | 200/well | 48.8 |
| CAL27 | 7 | 800/well | 23 |
| | 11 | 400/well | 15.3 |
| PE/CA-PJ34 C12 | 13 | 1000/well | 18.1 |
| | 10 | 2000/well | 13.6 |
| HSC-3 | 7 | 1500/well | 972 |
| | 11 | 750/well | 931 |

Modifications and variations in the subject matter set forth in the above illustrative examples are expected to occur to those skilled in the art. Only such limitations as appear in the appended claims should be placed on any claimed invention.

All publications including patents, patent applications and published patent applications cited herein are hereby incorporated by reference for all purposes.

What is claimed:

1. A crystalline form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt, where the crystalline form exhibits at least one of:
   a solid state $^{13}C$ NMR spectrum with peaks at 143.2, 136.0, 131.8, 123.9, 112.2, 105.2, and 100.3 ppm±0.2 ppm;
   a differential scanning calorimetry thermogram having an endotherm with a maximum at between about 320° C. and about 335° C.;
   a thermogravimetric analysis thermogram indicative of an unsolvated material;
   a dynamic vapor sorption isotherm plot which does not exhibit a significant weight change from 0 to 95% relative humidity;
   an X-ray powder diffraction pattern comprising characteristic peaks expressed in d-values (Å) of about 11.9, 5.9, 4.9, 4.4, 4.3, 3.9, and 3.7; and
   an X-ray powder diffraction pattern comprising peaks at 2θ angle degrees±0.2 2θ angle degrees of 7.4, 15.1, 18.1, 20.1, 20.4, 22.6, and 24.0.

2. The crystalline form of the (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one tosylate salt of claim 1, where the crystalline form has a purity of at least about 99.5%.

3. The crystalline form of the tosylate salt of claim 1, where the crystalline form is substantially free of an amorphous form of (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one or a salt or solvate thereof.

4. A pharmaceutical composition comprising the crystalline form of the tosylate salt according to claim 1 and a pharmaceutically acceptable excipient.

5. The pharmaceutical composition according to claim 4, where the composition is formulated for oral administration to a subject.

* * * * *